US011452706B2

(12) United States Patent
Lila et al.

(10) Patent No.: US 11,452,706 B2
(45) Date of Patent: Sep. 27, 2022

(54) METHODS AND COMPOSITIONS FOR ATTENUATING ALLERGENICITY IN PROTEIN PRODUCTS

(71) Applicant: NORTH CAROLINA STATE UNIVERSITY, Raleigh, NC (US)

(72) Inventors: Mary Ann Lila, Kannapolis, NC (US); Mary H. Grace, Concord, NC (US)

(73) Assignee: NORTH CAROLINA STATE UNIVERSITY, Raleigh, NC (US)

(*) Notice: Subject to any disclaimer, the term of this patent is extended or adjusted under 35 U.S.C. 154(b) by 942 days.

(21) Appl. No.: 15/524,087

(22) PCT Filed: Nov. 5, 2015

(86) PCT No.: PCT/US2015/059214
§ 371 (c)(1),
(2) Date: May 3, 2017

(87) PCT Pub. No.: WO2016/073702
PCT Pub. Date: May 12, 2016

(65) Prior Publication Data
US 2017/0333386 A1   Nov. 23, 2017

Related U.S. Application Data

(60) Provisional application No. 62/076,978, filed on Nov. 7, 2014.

(51) Int. Cl.
*A61K 31/35* (2006.01)
*A23L 33/105* (2016.01)
*B01D 11/02* (2006.01)
*C07D 311/62* (2006.01)
*A61K 39/35* (2006.01)

(52) U.S. Cl.
CPC ............ *A61K 31/35* (2013.01); *A23L 33/105* (2016.08); *B01D 11/02* (2013.01); *C07D 311/62* (2013.01); *A23V 2002/00* (2013.01); *A61K 39/35* (2013.01)

(58) Field of Classification Search
None
See application file for complete search history.

(56) References Cited

U.S. PATENT DOCUMENTS

| | | | |
|---|---|---|---|
| 8,173,178 B1 | 5/2012 | Ghaedian et al. | |
| 2002/0119946 A1 | 8/2002 | Gen | |
| 2008/0317891 A1* | 12/2008 | Anderson | A23G 1/32 424/776 |
| 2009/0035440 A1* | 2/2009 | Velikov | A61K 8/645 426/597 |
| 2010/0098789 A1* | 4/2010 | Balambika | A23L 33/105 424/756 |
| 2012/0269887 A1* | 10/2012 | Dreher | A61K 31/7048 424/451 |

FOREIGN PATENT DOCUMENTS

| | | |
|---|---|---|
| CN | 103289430 | 9/2013 |
| JP | 2005124540 | 5/2005 |
| WO | 2013/165455 | 11/2013 |
| WO | WO 2014011693 | 1/2014 |

OTHER PUBLICATIONS

California Olive Oil News, 2006, https://www.oliveoilsource.com/article/health-effects-polyphenols-virgin-olive-oil.*
2016 https://www.myfussyeater.com/easy-chocolate-peanut-clusters/#tasty-recipes-8916.*
The Paanut Institute, 2013, https://www.prnewswire.com/news-releases/eating-peanut-butterpeanuts-at-breakfast-helps-control-hunger-and-blood-sugar-all-day-211948191.html.*
Plundrich et al., Novel Strategy to Create Hypoallergenic Peanut Protein-Polyphenol Edible Matrices for Oral Immunotherapy, 2014, J Agric Food Chem, 62: 7010-7021.*
Plundrich, Nathalie et al. "Novel Strategy to Create Hypoallergenic Peanut Protein-Polyphenol Edible Matrices for Oral Immunotherapy", Journal of Agricultural and Food Chemistry, 62:7010-7021 (2014).
Schneider, Margaret et al. "Formation of whey protein-polyphenol mesostructures as a natural means of creating functional particles", Food & Function, 7(3):1306-1318 (2016).
Foegeding, E. Allen et al. "Protein-polyphenol particles for delivering structural and health functionality", Food Hydrocolloids, 72:163-173 (2017).
Plundrich, Nathalie et al. "Stability and immunogenicity of hypoallergenic peanut protein-polyphenol complexes during in vitro pepsin digestion", Food & Function, 6:2145-2154 (2015).
Lila, Mary Ann et al. "Polyphenol-enriched berry extracts naturally modulate reactive proteins in model foods", Food & Function, 8:4760-4767 (2017).
Foegeding, E. Allen et al. "Protein-polyphenol particles for delivering structural and health functionality", Food Hydrocolloids, 72:163-173 (2017).
Plundrich, Nathalie et al. "Stability and immunogenicity of hypoallergenic peanut protein-polyphenol complexes during in vitro pepsin digestion", Food & Function, 6:2145-2154 (2015).
Lila, Mary Ann et al. "Polyphenol-enriched berry extracts naturally modulate reactive proteins in model foods", Food & Function, 8:4760-4767 (2017).

(Continued)

Primary Examiner — Terry A McKelvey
Assistant Examiner — Catheryne Chen
(74) Attorney, Agent, or Firm — Myers Bigel, P.A.

(57) ABSTRACT

The invention relates to a low sugar or sugar free concentrated polyphenolic extract comprising at least about 30% polyphenols (w/w) and a protein-polyphenol aggregate matrix comprising at least about 15% polyphenols (w/w). The invention further relates to methods of producing a low sugar or sugar free concentrated polyphenolic extract comprising (a) extracting a low sugar or sugar free plant tissue with an aqueous solvent to produce an extract having an aqueous portion and a solids portion; (b) filtering the extract to separate the aqueous portion from the solids portion; and (c) reducing the volume of the separated aqueous portion, and methods of producing a protein-polyphenol aggregate matrix comprising about 1% to about 40% polyphenols (w/w) using the low sugar or sugar free concentrated polyphenolic extract of the invention.

20 Claims, 9 Drawing Sheets

(56) References Cited

OTHER PUBLICATIONS

Bansode, Rishipal R. et al. "Peanut flour aggregation with polyphenolic extracts derived from peanut skin inhibits IgE binding capacity and attenuates RBL-2H3 cells degranulation via MAPL signaling pathway", Food Chemistry, 263:307-314 (2018).

Plundrich, Nathalie et al. "Protein-bound Vaccinium fruit polyphenols decrease IgE binding to peanut allergens and RBL-2H3 mast cell degranulation in vitro", Food & Function, 8:1611-1621 (2017).

Written Opinion of the Internationa Search Report corresponding to International Application No. PCT/US2015/059214, dated Jan. 14, 2016, 10 pages.

Guevara-Aruaza J.C. et al., "Biofunctional activity of tortillas and bars enhanced with nopal. Preliminary assessment of functional effect after intake on the oxidative status in healthy volunteers.", *Chemistry Central Journal,* (2011), vol. 5, No. 10, pp. 1-10.

Roopchand D. E. et al., "Efficient sorption of polyphenols to soybean flour enables natural fortification of foods.", *Food Chemistry,* (2012), vol. 131, No. 4, pp. 1193-1200.

Sarker D.K. et al., "Control of sufarctant-induced destabilization of foams through polyphenol-mediated protein-protein interactions.", *J. Agric. Food Chem.,* (1995), vol. 43, No. 2, pp. 295-300.

Third Australian Examination Report, Australian Application No. 2015343046, dated Dec. 20, 2019, 10 pages.

Chung et al. "Reducing the allergenic capacity of peanut extracts and liquid peanut butter by phenolic compounds" Food Chemistry, 115:1345-1349 (2009).

* cited by examiner

Fig. 5A-B

METHODS AND COMPOSITIONS FOR ATTENUATING ALLERGENICITY IN PROTEIN PRODUCTS

STATEMENT OF PRIORITY

This application is a 35 U.S.C. § 371 national phase application of International Application Serial No. PCT/US2015/059214, filed Nov. 5, 2015, which claims the benefit, under 35 U.S.C. § 119 (a) of U.S. Provisional Patent Application No. 62/076,978 filed Nov. 7, 2014, the entire contents of each of which are incorporated by reference herein.

FIELD OF THE INVENTION

The invention relates to methods for producing highly enriched-protein-polyphenol aggregate matrices for use in allergy therapies, food supplements or ingredients, and attenuation of protein allergens in foods.

BACKGROUND OF THE INVENTION

Food allergies have a detrimental impact on quality of life, can present life-threatening consequences and are of increasing public health concern. Various food allergies are responsible for approximately 125,000 emergency room visits and 53,700 episodes of anaphylaxis each year in the USA alone (Decker et al., *J. Allergy Clin. Immunol.* 122: 1161-1165 (2008); Ross et al. *J. Allergy Clin. Immunol.* 121:166-171 (2008)). The term 'food allergy' is defined in the 2010 U.S. National Institutes of Allergy and Infectious Diseases (NIAID)-sponsored guidelines as an 'adverse health effect arising from a specific immune response that occurs reproducibly on exposure to a given food' (Boyce et al. *J. Allergy Clin. Immunol.* 126:S1-S58 (2010)).

The allergic reaction or adverse immune response occurs in response to certain proteins within a food called allergens or allergenic proteins. While harmless to most people, these allergens are recognized by sensitive individuals as harmful foreign material. Exposure to a food allergen results in a sensitization (towards the allergen) in susceptible individuals involving an immune response cascade with production of certain immune cells which recognize the allergen after re-exposure. This can lead to an allergic reaction (physical symptoms) upon consumption when segments of the allergenic edible proteins (epitopes) bind and cross link to allergen-specific immunoglobulin E (IgE) antibodies on mast cell and basophil surfaces, which trigger the downstream cascades responsible for the allergic response.

Over the last several decades, the prevalence and burden of food allergies has increased and become a worldwide health problem. Approximately 5% of young children and 3-4% of adults are affected by food allergy in westernized countries (Sicherer & Sampson, *J. Allergy Clin. Immunol.* 125:S116-S125 (2010)). More than 170 foods have been identified as potential causes for adverse immune responses and associated symptoms and disorders (involving the skin and gastrointestinal and respiratory tracts); however, only a minority of these foods cause the majority of reactions (Boyce et al. *J. Allergy Clin. Immunol.* 126:S1-S58 (2010)). Over 90% of food allergies are triggered by milk, egg, peanut, tree nuts, shellfish, fish, wheat or soy; yet, common food allergens vary between geographical regions (Hefle et al., *Crit. Rev. Food Sci.* 36:S69-S89 (1996)).

The overall incidence of food allergies is increasing, affecting quality of life for afflicted individuals, and creating serious public health concerns. For these reasons, there is interest in developing therapeutic strategies that could alleviate the danger and severity of IgE-mediated or immune cell mediated allergic reactions. Numerous processing and non-processing strategies to mitigate allergy have been investigated including 1) thermal and non-thermal food processing techniques, 2) enzymatic hydrolysis, 3) controlled Maillard modifications, 4) genetic engineering/biotechnological methods to alter the edible protein, 5) non-allergen-specific immunomodulation by dietary phytochemicals, and 6) allergen-specific immunotherapy approaches (oral immunotherapy and sublingual immunotherapy). Many of these tactics modulate allergenicity by altering IgE binding epitopes (the allergenic segments of edible proteins), but to date, none of the intervention methods aimed at alleviating immune disorders towards food proteins have proven to be practical, efficient, or food-grade compliant enough to facilitate widespread acceptance by medical practitioners or consumers.

SUMMARY OF THE INVENTION

In one aspect, a low sugar or sugar free concentrated polyphenolic extract is provided comprising at least about 30% polyphenols (w/w based on dry weight).

In another aspect, a protein-polyphenol aggregate matrix is provided comprising at least about 15% polyphenols (w/w based on dry weight).

In a further aspect, a method of producing a low sugar or sugar free concentrated polyphenol extract is provided, comprising (a) extracting a low sugar or sugar free plant tissue with an aqueous solvent to produce a mixture having an aqueous portion and a solids portion; (b) filtering the mixture to separate the aqueous portion from the solids portion; and (c) reducing the volume of the separated aqueous portion to produce a low sugar or sugar free concentrated polyphenolic extract.

In an additional aspect of the invention, a method is provided for producing a protein-polyphenol aggregate matrix comprising about 1% to about 40%, optionally at least about 15% polyphenols, the method comprising: contacting a low sugar or sugar free concentrated polyphenolic extract of the invention with a protein product to produce a protein-polyphenol complexed product; and dehydrating protein-polyphenol complexed product to produce a protein-polyphenol aggregate matrix.

In another aspect, the invention provides a method of attenuating an allergic response in a subject in need thereof, comprising administering to the subject a protein-polyphenol aggregate matrix of the invention.

In a further aspect, the invention provides a method of producing a food product having reduced reactivity of a protein component, comprising adding the protein-polyphenol aggregate matrix of the invention to a composition for the production of the food product, thereby producing a food product having reduced reactivity of the protein component.

In an additional aspect, producing a high protein bar having reduced hardening, comprising adding the protein-polyphenol aggregate matrix of the invention to a composition for the production of the high protein bar, thereby producing a high protein bar having reduced hardening.

These and other aspects of the invention are set forth in more detail in the description of the invention below.

DETAILED DESCRIPTION

Figure 1:
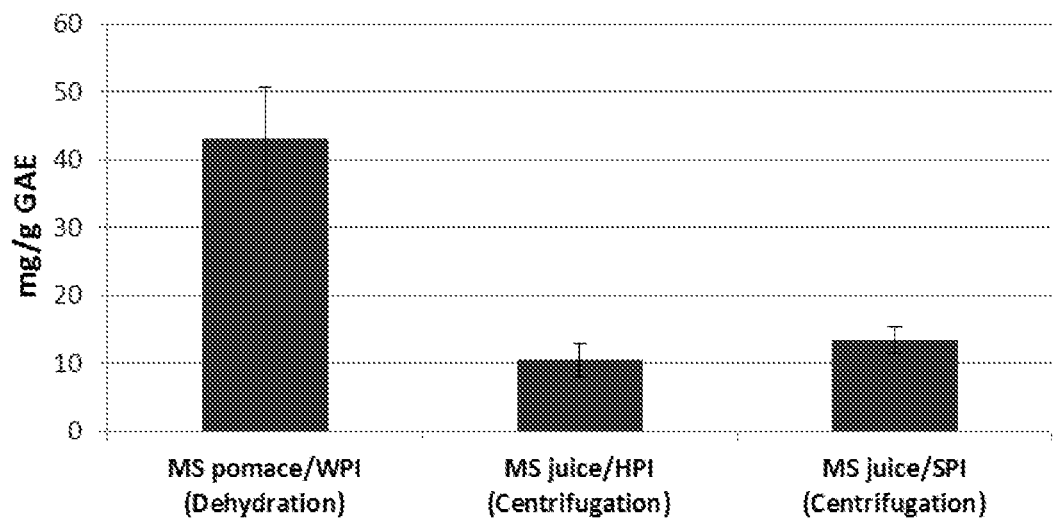
FIG. 1 shows total phenolics that complexed into protein-polyphenol aggregate matrices using the methods of the invention (left bar) and an art known method (middle and right bars). WPI=whey protein isolate, HPI=hemp protein isolate, SPI, soy protein isolate, MS muscadine grape; GAE=gallic acid equivalent.

The present invention now will be described hereinafter with reference to the accompanying drawings and examples, in which embodiments of the invention are shown. This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. Thus, the invention contemplates that in some embodiments of the invention, any feature or combination of features set forth herein can be excluded or omitted. In addition, numerous variations and additions to the various embodiments suggested herein will be apparent to those skilled in the art in light of the instant disclosure, which do not depart from the instant invention. Hence, the following descriptions are intended to illustrate some particular embodiments of the invention, and not to exhaustively specify all permutations, combinations and variations thereof.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

All publications, patent applications, patents and other references cited herein are incorporated by reference in their entireties for the teachings relevant to the sentence and/or paragraph in which the reference is presented.

Unless the context indicates otherwise, it is specifically intended that the various features of the invention described herein can be used in any combination. Moreover, the present invention also contemplates that in some embodiments of the invention, any feature or combination of features set forth herein can be excluded or omitted. To illustrate, if the specification states that a composition comprises components A, B and C, it is specifically intended that any of A, B or C, or a combination thereof, can be omitted and disclaimed singularly or in any combination.

As used in the description of the invention and the appended claims, the singular foul's "a," "an" and "the" are intended to include the plural forms as well, unless the context clearly indicates otherwise.

Also as used herein, "and/or" refers to and encompasses any and all possible combinations of one or more of the associated listed items, as well as the lack of combinations when interpreted in the alternative ("or").

The term "about," as used herein when referring to a measurable value such as a dosage or time period and the like refers to variations of ±20%, ±10%, ±5%, ±1%, ±0.5%, or even ±0.1% of the specified amount.

As used herein, phrases such as "between X and Y" and "between about X and Y" should be interpreted to include X and Y. As used herein, phrases such as "between about X and Y" mean "between about X and about Y" and phrases such as "from about X to Y" mean "from about X to about Y."

The term "comprise," "comprises" and "comprising" as used herein, specify the presence of the stated features, integers, steps, operations, elements, and/or components, but do not preclude the presence or addition of one or more other features, integers, steps, operations, elements, components, and/or groups thereof.

As used herein, the transitional phrase "consisting essentially of" means that the scope of a claim is to be interpreted to encompass the specified materials or steps recited in the claim and those that do not materially affect the basic and novel characteristic(s) of the claimed invention. Thus, the term "consisting essentially of" when used in a claim of this invention is not intended to be interpreted to be equivalent to "comprising."

As used herein, "contact," contacting," "contacted," and grammatical variations thereof, refers to placing the components of a desired reaction together under conditions suitable for carrying out the desired reaction (e.g., extracting, complexing, adsorbing, binding, and the like).

As used herein, the terms "increase," "increasing," "increased," "enhance," "enhanced," "enhancing," and "enhancement" (and grammatical variations thereof) describe an elevation of at least about 5%, 10%, 15%, 20%, 25%, 50%, 75%, 100%, 150%, 200%, 300%, 400%, 500%, 750%, 1000%, 2500%, 5000%, 10,000%, 20,000% or more as compared to a control (e.g., the concentration of a polyphenol extract prepared by a method other than that described herein; the amount of polyphenols in a protein-polyphenol aggregate matrix prepared using a polyphenol extract other than that described herein; or a food product (therapeutic or non-therapeutic not prepared using protein-polyphenol aggregates of the invention).

As used herein, the terms "reduce," "reduced," "reducing," "reduction," "diminish," "suppress," and "decrease" (and grammatical variations thereof), describe, for example, a decrease of at least about 5%, 10%, 15%, 20%, 25%, 35%, 50%, 75%, 80%, 85%, 90%, 95%, 97%, 98%, 99%, or 100% as compared to a control. In particular embodiments, the reduction results in no or essentially no (i.e., an insignificant amount, e.g., less than about 10% or even less than about 5%) detectable activity or amount (e.g., reduced allergic response, or reduced protein reactivity).

Dietary phytochemicals, such as polyphenols, have shown potential for preventing and ameliorating allergic reactions including food allergies (Nowak-Wegrzn & Sampson, *J. Allergy Clin. Immunol.* 128:558-573 (2011)). Purified smaller molecular weight chemicals administered alone (quercetin, catechin monomers, luteolin) have partially attenuated allergic reactions (Singh et al., *Clin. Exp. Allergy* 41:1346-1359 (2011)). A mixture of phytoactives (bioactive polyphenolics) from nine different herbs in a Chinese herbal medicine called Food Allergy Herbal Formula 2 (FAHF 2) was able to suppress anaphylactic symptoms in peanut allergic mice challenged monthly with peanut for up to 6 months (Qu et al., *Clin. Exp. Allergy* 37:846-855 (2007)). Mechanisms of immunomodulation for phytoactives are diverse and include: direct inhibition of mast cell mediator release; suppression of T cell proliferation; inhibition of Th2 cytokine secretion; and decreased allergen specific-IgE production (Song et al. *J. Allergy Clin. Immunol.* 126:1208-1217 (2010); Srivastava et al. *J. Allergy Clin. Immunol.* 115:171-178 (2005)).

The present invention is directed to a novel method of preparing low sugar or sugar free concentrated polyphenols extracts and their use in, for example, the preparation of food supplements as well as protein-polyphenol aggregate matrices for general consumption and use in attenuating allergic response (immunotherapy).

Accordingly, in a first aspect, a low sugar or sugar free concentrated polyphenol extract is provided comprising, consisting essentially of, or consisting of at least about 30% (w/w) polyphenols. In some embodiments, a low sugar or sugar free concentrated polyphenol extract is provided comprising, consisting essentially of, or consisting of about 30% to about 75% polyphenols (w/w). In some embodiments, the low sugar or sugar free concentrated polyphenol extract comprises, consists essentially of, or consists of at least about 30% to about 70%, about 30% to about 65%, about 30% to about 60%, about 30% to about 50%, about 30% to about 40%, about 35% to about 75%, about 35% to about 70%, about 35% to about 60%, about 35% to about 50%, about 40% to about 75%, about 40% to about 70%, about 40% to about 65%, about 40% to about 60%, about 40% to about 50%, about 50% to about 75%, about 50% to about 70%, about 50% to about 65%, about 50% to about 60% polyphenols (w/w), and the like. Therefore, in some embodiments, the low sugar or sugar free concentrated polyphenolic extract comprises, consists essentially of, or consists of at least about 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75 percent (w/w), or any value or range therein, of polyphenols.

As used herein, "low sugar" refers to an extract that is very low in sugar (e.g., less than 10%, less than 9%, less than 8%, less than 7%, less than 6%, less than 5%, less than 4%, less than 3%, less than 2%, less than 1%), which would not interfere with the binding/complexation of proteins and polyphenols. In some embodiments, a low sugar extract of the invention can comprise, consist essentially of, or consist of less than 10% sugars or about 10% to about 1% sugars (e.g., about 10, 9, 8, 7, 6, 5, 4, 3, 2, 1% sugars, or an range or value therein). As used herein, "sugar free" refers to an extract that is essentially free of sugars (e.g., less than 1% sugars to no sugars). In representative embodiments, a low sugar or sugar free extract of the invention can comprise, consist essentially of, or consist of less than 1% sugars. The extracts are low in or free of sugars known to be present in fruits and vegetables including but not limited to sucrose, fructose, glucose, galactose, and the like. Sugars that are integral parts of a molecule, for example, a glycosylated anthocyanin, are not included in this definition.

In a further aspect, a protein-polyphenol aggregate matrix is provided that comprises, consists essentially of, or consists of about 1% to about 75% polyphenols (w/w), optionally at least about 15% polyphenols (w/w). In some embodiments, the protein-polyphenol aggregate matrix comprises, consists essentially of, or consists of about 1% to about 70%, about 1% to about 60%, about 1% to about 50%, about 1% to about 35%, about 1% to about 30%, 1% to about 25%, about 1% to about 20%, about 1% to about 15%, about 1% to about 10%, about 1% to about 5%, about 5% to about 70%, about 5% to about 60%, about 5% to about 50%, about 5% to about 40%, about 5% to about 35%, about 5% to about 30%, about 5% to about 25%, about 5% to about 20%, about 5% to about 15%, about 5% to about 10%, about 10% to about 70%, about 10% to about 60%, about 10% to about 50%, about 10% to about 40%, about 10% to about 35%, about 10% to about 30%, about 10% to about 25%, about 10% to about 20%, about 10% to about 15%, about 15% to about 70%, about 15% to about 60%, about 15% to about 50%, about 15% to about 40%, about 15% to about 35%, about 15% to about 30%, about 15% to about 25%, about 15% to about 20%, about 20% to about 70%, about 20% to about 60%, about 20% to about 50%, about 20% to about 40%, about 20 to about 35%, about 20 to about 30%, about 20% to about 25%, about 25% to about 40%, about 25% to about 35%, about 25% to about 30%, about 30% to about 70%, about 30% to about 60%, about 30% to about 50%, about 30 to about 40%, about 30 to about 35%, about 35% to about 40% (w/w), and the like. In representative embodiments, a protein-polyphenol aggregate matrix is provided that comprises, consists essentially of, or consists of at least about 15% polyphenols (w/w). Therefore, in some embodiments, the protein-polyphenol aggregate matrix comprises, consists essentially of, or consists of at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75 percent (w/w), or any value or range therein, of polyphenols. In representative embodiments, the protein-polyphenol aggregate matrix comprises, consists essentially of, or consists of or about 1% to about 40% polyphenols (w/w).

Any protein product for which a need for attenuating allergenicity has been identified can be used with the methods of the invention. In some embodiments, the protein of a protein-polyphenol aggregate matrix of the invention can include, but is not limited to, peanut, tree nut, milk, whey, egg, soy, fish, shellfish, rice, wheat, or any combination thereof. In some embodiments, the protein-polyphenol aggregate matrix can include, but is not limited to, a yogurt, an applesauce, an immunotherapeutic protein product, and the like. In some embodiments, when producing a food product not intended for attenuating allergenicity, the protein of a protein-polyphenol aggregate matrix can be any protein source.

Thus, in some embodiments, a protein-polyphenol aggregate matrix can be an immunotherapeutic protein product comprising, consisting essentially of, or consisting of about 5% to about 75% polyphenols. In some embodiments, the immunotherapeutic protein product comprises, consists essentially of, or consists of at least about 5% to about 70%, about 5% to about 60%, about 5% to about 50%, about 5% to about 40%, about 5% to about 35%, about 5% to about 30%, about 5% to about 25%, about 5% to about 20%, about 5% to about 15%, about 5% to about 10%, about 10% to about 75%, about 10% to about 70%, about 10% to about 60%, about 10% to about 50%, about 10% to about 40%, about 10% to about 35%, about 10% to about 30%, about 10% to about 25%, about 10% to about 20%, about 10% to about 15%, about 15% to about 75%, about 15% to about 70%, about 15% to about 60%, about 15% to about 50%, about 15% to about 40%, about 15% to about 35%, about 15% to about 30%, about 15% to about 25%, about 15% to about 20%, about 20% to about 75%, about 20% to about 70%, about 20% to about 60%, about 20% to about 50%, about 20% to about 40%, about 20 to about 35%, about 20 to about 30%, about 20% to about 25%, about 25% to about 75%, about 25% to about 70%, about 25% to about 60%, about 25% to about 50%, about 25% to about 40%, about 25% to about 35%, about 25% to about 30%, about 30% to about 75%, about 30% to about 70%, about 30% to about 60%, about 30% to about 50%, about 30 to about 40%, about 30 to about 35%, about 35% to about 40% (w/w), and the like. In representative embodiments, the protein-polyphenol aggregate matrix can be an immunotherapeutic protein product comprising, consisting essentially of, or consisting of about 5% to about 40% polyphenols (w/w) or about 30% to about 40% polyphenols (w/w). Thus, in some embodiments, the immunotherapeutic protein product comprises, consists essentially of, or consists of at least about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75 percent (w/w), or any value or range therein, of polyphenols.

Thus, in other embodiments, a protein-polyphenol aggregate matrix can be a protein food product (e.g., therapeutic and non-therapeutic food products) comprising, consisting essentially of, or consisting of about 0.1% to about 75% polyphenols, optionally about 0.1% to about 40% polyphenols. In some embodiments, the protein food product comprises, consists essentially of, or consists of about 0.1% to about 70%, about 0.1% to about 60%, about 0.1% to about 50%, about 0.1% to about 35%, about 0.1% to about 30%, about 0.1% to about 25%, about 0.1% to about 20%, about 0.1% to about 15%, about 0.1% to about 10%, about 0.1% to about 5%, about 0.1% to about 0.5%, about 0.1% to about 0.2%, about 0.2% to about 70%, about 0.2% to about 60%, about 0.2% to about 50%, about 0.2% to about 60%, about 0.2% to about 30%, about 0.2% to about 25%, about 0.2% to about 20%, about 0.2% to about 15%, about 0.2% to about 10%, about 0.2% to about 5%, about 0.2% to about 0.5%, about 0.5% to about 70%, about 0.5% to about 60%, about 0.5% to about 50%, about 0.5% to about 60%, about 0.5% to about 30%, about 0.5% to about 25%, about 0.5% to about 20%, about 0.5% to about 15%, about 0.5% to about 10%, about 0.5% to about 5%, about 1% to about 70%, about 1% to about 60%, about 1% to about 50%, about 1% to about 40%, about 1% to about 35%, about 1% to about 30%, 1% to about 25%, about 1% to about 20%, about 1% to about 15%, about 1% to about 10%, about 1% to about 5%, about 5% to about 70%, about 5% to about 60%, about 5% to about 50%, about 5% to about 40%, about 5% to about 35%, about 5% to about 30%, about 5% to about 25%, about 5% to about 20%, about 5% to about 15%, about 5% to about 10%, about 10% to about 70%, about 10% to about 60%, about 10% to about 50%, about 10% to about 40%, about 10% to about 35%, about 10% to about 30%, about 10% to about 25%, about 10% to about 20%, about 10% to about 15%, about 15% to about 70%, about 15% to about 60%, about 15% to about 50%, about 15% to about 40%, about 15% to about 35%, about 15% to about 30%, about 15% to about 25%, about 15% to about 20%, about 20% to about 70%, about 20% to about 60%, about 20% to about 50%, about 20% to about 40%, about 20 to about 35%, about 20 to about 30%, about 20% to about 25%, about 25% to about 40%, about 25% to about 35%, about 25% to about 30%, about 30% to about 70%, about 30% to about 60%, about 30% to about 50%, about 30 to about 40%, about 30 to about 35%, about 35% to about 40% (w/w), and the like, and the like. Thus, in some embodiments, the protein food product comprises, consists essentially of, or consists of at least about 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75 percent (w/w), or any value or range therein, of polyphenols. In representative embodiments, the protein food product comprises, consists essentially of, or consists of about 0.1% to about 40% polyphenols (w/w).

In some embodiments, a method of producing a low sugar or sugar free concentrated polyphenolic extract is provided, comprising: (a) extracting a low sugar or sugar free plant tissue with an aqueous solvent to produce a mixture having an aqueous portion and a solids portion; (b) filtering the mixture to separate the aqueous portion from the solids portion; and (c) reducing the volume of the separated aqueous portion to produce a low sugar or sugar free concentrated polyphenolic extract.

In some embodiments, the low sugar or sugar free plant tissue comprises, consists essentially of, or consists of a pomace and/or a fermented fruit product. "Pomace" as used herein means the pulpy tissue remaining after fruit and/or other plant material, including seeds, leaves, etc., has been crushed in order to extract the juice. Any polyphenol rich fruit or vegetable that is commercially juiced can be used, including but not limited to any type of berry. In some embodiments, a pomace can be from a plant including, but not limited to, apple, pomegranate, black currant, blueberry, cranberry, lingnonberry, cherry, grape, muscadine, blackberry, chokecherry (aroma), cinnamon, *Sorbaronia mitschurinii*, *Camellia* spp. (tea) (e.g., *Camellia sinensis*, *Camellia oleifera*), and/or peanut (*Arachis hypogaea*) (e.g., peanut skins).

In some embodiments, the low sugar or sugar free plant tissue is not a fruit juice. As is well known in the art, fruit juice is not low sugar or sugar free. Notably, the high levels of sugars in fruit juice, which would naturally end up in a polyphenol extract prepared using the fruit juice, can interfere with the ability of the polyphenols to bind with the proteins of the protein products. Use of low sugar and sugar free plant tissue allows more precise control of the binding as well as the concentrations of polyphenols and proteins, which is important for allergenicity applications. However, in other embodiments, when the product is a food product not necessarily for use in amelioration of allergic response, such as for food functionality applications (e.g., enhanced foam strength or diminished bar hardening), fruit juices that are not sugar free or low sugar may be used as a polyphenol source. For example, juices can be used in producing a nutrition bars and shakes (e.g., high protein bars and shakes).

Fermentation is a process in which an agent, such as a fungus and/or a bacterium, causes an organic substance to break down into simpler substances; and includes the anaerobic breakdown of sugar into alcohol. A "fermented fruit product" as used herein is a product of a fermentation process. Any polyphenol rich plant (e.g., fruit or vegetable) can be used with this invention. In some embodiments, any polyphenol rich fruit or vegetable that is commercially juiced can be used. For example, any type of berry may be used with this invention. Non-limiting examples of plants useable as a source of polyphenols can be black currant, blueberry, cranberry, lingnonberry, cherry, grape, muscadine, blackberry, green tea (*Camellia* spp.), cinnamon, *aronia*, *Sorbaronia mitschurinii*, citrus, and/or peanut (e.g., peanut skins). In some embodiments, a fermented fruit product can be from a plant including, but not limited to, black currant, blueberry, cranberry, lingnonberry, cherry, grape, muscadine, blackberry, green tea (*Camellia* spp.), cinnamon, *aronia*, *Sorbaronia mitschurinii*, citrus, peanut (e.g., peanut skins), or any combination thereof.

Thus, low sugar or sugar free plant tissue is contacted with an aqueous solvent to extract the polyphenols into the solvent fraction and then the extract is filtered to separate the aqueous extract (polyphenol rich) portion from any remaining solids.

In some embodiments, the aqueous solvent can be any food grade aqueous solvent. In some embodiments, the aqueous solvent can be water. In some embodiments, the food grade solvent can be a food grade alcohol. In some embodiments, the aqueous solvent is present at a concentration of about 1% to about 70% (v/v). In some embodiments, the aqueous solvent can present at a concentration in the range of about 5% to about 65%, about 10% to about 60%, about 10% to about 50%, about 10% to about 40%, about 10% to about 30%, about 15% to about 60%, about 15% to about 55%, about 15% to about 50%, about 15% to about 40%, about 20% to about 70%, about 20% to about 60%, about 20% to about 50%, about 20% to about 40%, about 20% to about 30%, about 25% to about 45%, about 30% to about 70%, about 30% to about 60%, about 30% to about 50%, about 30% to about 40%, about 40% to about 70%, about 40% to about 60%, about 40% to about 50%, about 50% to about 70%, about 50% to about 65%, about 50% to about 60% (v/v), and the like. Thus, in some embodiments, the aqueous solvent is present at a concentration of about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70% (v/v), or any range or value therein.

In some embodiments, the food grade alcohol can be a food grade ethanol. In particular embodiments, the concentration of the food grade ethanol can be about 30% to about 60%, about 30% to about 50%, about 30% to about 40%, about 40% to about 60%, about 40% to about 50%, about 50% to about 65%, about 50% to about 60% (v/v), and the like. Accordingly, in some embodiments, the concentration of the food grade ethanol can be about 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60% (v/v), or any range or value therein. In representative embodiments, the concentration of the ethanol can be about 50 percent.

The skilled artisan will understand that the choice of aqueous solvent may depend on the source of pomace or fermented fruit product. Thus, for example, for extraction of pomace or fermented product from cinnamon, the aqueous solvent will likely be a mixture of water and food grade ethanol. However, for many other pomaces and fermented fruit products water alone can be effective for extraction of the polyphenols. Large volumes of plant material can be extracted with small volumes of aqueous solvent including water to provide a sufficient yield of polyphenols. Thus, for example, because pomace is generally a waste product and is thus an inexpensive source of polyphenols, the ratio of plant material (e.g., pomace) to aqueous solvent can be quite high without a loss of efficiency in the process. Further, the amount of aqueous solvent used to extract the low sugar or sugar free plant tissue may be affected by the nature of the low sugar or sugar free plant tissue. Thus, as would be understood by the skilled artisan, a ratio of solvent to the plant tissue is used such that the tissue will be sufficiently solubilized/covered with solvent. Accordingly, also as would be well understood by the skilled artisan, a lower ratio of solvent to low sugar or sugar free plant tissue can be used with those sources of low sugar or sugar free plant tissue that comprise more liquid (e.g., fermented fruit product) than those sources that are more dry (e.g., pomace).

Thus, in some embodiments, the ratio of low sugar or sugar free plant tissue to aqueous solvent can be in a range of about 1:5 to about 1:10 (w/v). Thus, in some embodiments, the ratio of low sugar or sugar free plant tissue to aqueous solvent can be about 1:5, 1:6, 1:7, 1:8, 1:9, 1:10 (w/v), or any range of ratios or any particular ratio, therein. In representative embodiments, the ratio of low sugar or sugar free plant tissue to aqueous solvent can be at least about 1:5 (w/v).

Any method for reducing the volume of a separated aqueous portion can be used. Such methods are well known in the art of food production (see, e.g., Saravacos et al. *New York's Food Life Sci. Bull.* 4:1-14 (1970)). In representative embodiments, reducing the volume of the separated aqueous portion comprises evaporation, optionally vacuum evaporation.

In some embodiments, a method of producing a low sugar or sugar free concentrated polyphenolic extract can optionally comprise heating the low sugar or sugar free plant tissue and aqueous solvent. In some embodiments, heating can increase the solubility of polyphenols in aqueous solvents such as ethanol, thereby maximizing the extraction process. Thus, in some embodiments, when extracting comprises heating, the heating can be for about 15 minutes to about 5 hours. In some embodiments, the heating can be for about 15 min to about 4 hours, about 30 min to about 5 hours, about 30 min to about 4 hours, about 30 min to about 3 hours, about 30 min to about 2 hours, about 30 min to about 1 hour, about 45 min to about 5 hours, about 45 min to about 4 hours, about 45 min to about 3 hours, about 45 min to about 2 hours, about 45 min to about 2.5 hours, about 1 hour to about 5 hours, about 1 hour to about 4 hours, about 1 hour to about 3 hours, about 1 hour to about 2 hours, about 1.5 hours to about 5 hours, about 1.5 hours to about 4 hours, about 1.5 hours to about 3 hours, about 1.5 hours to about 2 hours, or any range or value therein. Thus, in some embodiments, the heating can be for about 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59 minutes, or 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5 hours, or any range or value therein. In representative embodiments, the heating is for about 2 to about 3 hours, or any range or value therein. In some embodiments, the heating can be for about 2 hours.

In some embodiments, the heating comprises a temperature of about 80° C. or less. In some embodiments, the heating comprises a temperature in the range of about 70° C. to about 80° C. Thus, in some embodiments, the heating comprises a temperature of about 50, 51, 52, 53, 54, 55, 5, 57, 58, 59, 60, 61, 62, 63, 64, 65, 66, 67, 68, 69, 70, 71, 72, 73, 74, 75, 76, 77, 78, 79, 80° C., or any range or value therein.

While it has been observed that polyphenols can be protected to some degree from degradation due to high temperatures by complexation of polyphenols to protein, as in the present process, as would be understood by the skilled artisan, too much heat can destroy polyphenols. Thus, the range of time for heating will depend on the temperature used. Thus, higher temperatures can be used for shorter times and conversely, lower temperatures can be used with longer extraction times (i.e., time is inversely proportional to temperature).

In some embodiments, the method of producing a low sugar or sugar free concentrated polyphenolic extract can further optionally comprise, consist essentially of, or consist of (d) contacting the low sugar or sugar free concentrated polyphenolic extract with a resin; (e) washing the resin with water; (f) eluting the polyphenols from the resin with food grade alcohol to produce an alcohol polyphenol extract; and (g) evaporating the alcohol in the alcohol polyphenol extract to produce a concentrated polyphenol extract. In some embodiments, the amount of alcohol remaining in the concentrated polyphenol extract after evaporating can be about less than 5% (e.g., less than 5, 4.9, 4.8, 4.7, 4.6, 4.5, 4.4, 4.3, 4.2, 4.1, 4, 3.9, 3.8, 3.7, 3.6, 3.5, 3.4, 3.3, 3.2, 3.1, 3, 2.9, 2.8, 2.7, 2.6, 2.5, 2.4, 2.3, 2.2, 2.1, 2, 1.9, 1.8, 1.7, 1.6, 1.5, 1.4, 1.3, 1.2, 1.1, 1, 0.9, 0.8, 0.7, 0.6, 0.5, 0.4, 0.3, 0.2, 0.1, 0.09, 0.08, 0.07, 0.06, 0.05, 0.04, 0.03, 0.02, 0.01, 0.009, 0.008, 0.007, 0.006, 0.005, 0.004, 0.003, 0.002, 0.001% and the like and any range or value therein). In representative embodiments, the amount of alcohol remaining in the concentrated polyphenol extract after evaporating can be about less than 0.01% (e.g., 0.01, 0.009, 0.008, 0.007, 0.006, 0.005, 0.004, 0.003, 0.002, 0.001%, and the like, and any range or value therein).

In some embodiments, the food grade alcohol is food grade ethanol. In some embodiments, the food grade alcohol can be at a concentration of about 50 to about 100% (e.g., 50, 51, 52, 53, 54, 55, 5, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100%, and any range or value therein). Thus, in some embodiments, the food grade alcohol can be at a concentration of about 60% to about 100%, about 70% to about 100%, about 80% to about 100%, about 90% to about 100%, about 95% to about 100%, or any range or value therein.

In some embodiments, when the amount of sugars in the extract is, for example, greater than about 1%, the extract can be further contacted with a resin. In some embodiments, the ion exchange resin can be any non-polar polystyrene resins (e.g., polymeric adsorbents) for removing organic compounds from aqueous solutions. In some embodiments, the ion exchange resin can include but is not limited to AMBERLITE®, TOYOPEARL®, AMBERLITE XDA, Dowex Optipore and/or DIAION® HP 50. In other embodiments, the ion exchange resin can be, but is not limited to, a C18 SPE (solid phase extraction) cartridge. The contacting of the concentrated polyphenolic extract with a resin can comprises stirring and/or swirling the concentrated polyphenolic extract with the ion exchange resin. In some embodiments, contacting the concentrated polyphenolic extract with a resin comprises can comprise, consists essentially of, or consists of being still or stationary. In some embodiments, contacting the concentrated polyphenolic extract with a resin can comprise, consist essentially of, or consists of a combination of still, stirring and/or swirling. In some embodiments, contacting the polyphenolic extract with a resin comprises, consists essentially of, or consists of contacting for about 5 minutes to about 1 hour (e.g., about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60 minutes).

In some embodiments, washing the resin comprises washing at least about two times (e.g., 2, 3, 4, 5, 6, 7, 8, 9, 10 times or more, with water). In some embodiments, washing comprises washing the resin about two times to about ten times with water (e.g., 2, 3, 4, 5, 6, 7, 8, 9, or 10 times with water). In some embodiments, the total amount of water used to wash the resin can be no more than about 10 times the resin volume (e.g., 1, 2, 3, 4, 5, 6, 7, 8, 9, 10, and any range or value therein of water to resin volume). In some embodiments, the total amount of water used to wash the resin can be about 8 times to about 10 times the resin volume (e.g., 8, 9, 10 times the resin volume, or any range or value therein).

In some embodiments, a more acidic pH of the extract can be useful to tighten the binding between the polyphenols and proteins (e.g., to create more covalent irreversible bonds). Thus, in some embodiments, the pH of the low sugar or sugar free concentrated polyphenolic extract can adjusted to about pH 4 to about pH 5 (e.g., pH 4, 4.1, 4.2, 4.3, 4.4, 4.5, 4.6, 4.7, 4.8, 4.9, 5 and any range or value therein).

In some embodiments, the low sugar or sugar free concentrated polyphenolic extract can be contacted with a polyphenol oxidase (e.g., tyrosinase). In some embodiments, the low sugar or sugar free concentrated polyphenolic extract is contacted with a polyphenol oxidase (e.g., tyosinase) prior to adjusting the pH.

The invention further provides low sugar or sugar free concentrated polyphenolic extracts produced by the methods described herein comprising, consisting essentially of, or consisting of at least about 30% polyphenols (w/w). In some embodiments, a low sugar or sugar free concentrated polyphenolic extract comprises, consists essentially of, or consists of at least about 30 to about 75% polyphenols (w/w). In some embodiments, a low sugar or sugar free concentrated polyphenolic extract comprises, consists essentially of, or consists of about 30% to about 70%, about 30% to about 65%, about 30% to about 60%, about 30% to about 50%, about 30% to about 40%, about 35% to about 75%, about 35% to about 70%, about 35% to about 60%, about 35% to about 50%, about 40% to about 75%, about 40% to about 70%, about 40% to about 65%, about 40% to about 60%, about 40% to about 50%, about 50% to about 75%, about 50% to about 70%, about 50% to about 65%, about 50% to about 60% (w/w) polyphenols, and the like. Therefore, in some embodiments, the low sugar or sugar free concentrated polyphenolic extract comprises, consists essentially of, or consists of at least about 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75 percent (w/w), or any value or range therein, of polyphenols.

The filtered extract can then be used, for example, as a treatment intervention (e.g., a supplement that can be used by a clinician) or as an ingredient in a food product or dietary supplement. For treatment interventions, the forms can be the aggregate matrix mixed into applesauce or yogurt, etc. For food applications, the high concentration polyphenol product can be provided as a powdered (pill or capsule form or other) dietary supplement or it may be an ingredient incorporated into a food product. Thus, the concentrations and ratios of the aqueous solvent to the low sugar or sugar free plant tissue can vary according to the plant polyphenol.

Thus, in further embodiments, the invention provides a method of producing a protein-polyphenol aggregate matrix comprising, consisting essentially of, consisting of about 1% to about 40% polyphenols, the method comprising: contacting a low sugar or sugar free concentrated polyphenolic extract with a protein product to produce a protein-polyphenol complexed product; and dehydrating the protein-polyphenol complexed product to produce a protein-polyphenol aggregate matrix comprising, consisting essentially of, consisting of at least about 1% to about 40% polyphenols.

A protein-polyphenol aggregate matrix may be highly enriched in polyphenolics and the amount of phenolics that is sorbed onto the protein can be controlled using the methods of the invention. Notably, the protein-polyphenol aggregate matrix can be created having a gradient or range of polyphenol concentrations. Such gradients can be useful in, for example, desensitization of patients having allergies. The dosage and time between dosing and duration of dosing will vary for each subject treated for allergic reaction.

In some embodiments, the polyphenol concentration in the low sugar or sugar free concentrated polyphenolic extract can comprise, consist essentially of, consist of at least about 30% (w/w) polyphenols. In some embodiments, the polyphenol concentration in the low sugar or sugar free concentrated polyphenolic extract can comprise, consist essentially of, consist of about 30% to about 75% (w/w) polyphenols. Thus, in some embodiments, the polyphenol concentration in the low sugar or sugar free concentrated polyphenolic extract can comprise, consist essentially of, consist of about 30% to about 70%, about 30% to about 65%, about 30% to about 60%, about 30% to about 50%, about 30% to about 40%, about 35% to about 75%, about 35% to about 70%, about 35% to about 60%, about 35% to about 50%, about 40% to about 75%, about 40% to about 70%, about 40% to about 65%, about 40% to about 60%, about 40% to about 50%, about 50% to about 75%, about 50% to about 70%, about 50% to about 65%, about 50% to about 60% (w/w), and the like. Thus, in some embodiments, polyphenol concentration in the low sugar or sugar free concentrated polyphenolic extract can comprise, consist essentially of, consist of about 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75%, or any range or value therein. In representative embodiments, the polyphenol concentration in the low sugar or sugar free concentrated polyphenolic extract can comprise, consist essentially of, consist of about 30-60% (w/w) polyphenols.

In some embodiments, the low sugar or sugar free concentrated polyphenolic extract can be produced from low sugar or sugar free plant tissue. In some embodiments, the low sugar or sugar free plant tissue comprises, consists essentially of, or consists of a pomace and/or a fermented fruit product. Any polyphenol rich fruit or vegetable that is commercially juiced can be used for a pomace and/or a fermented fruit product, including but not limited to any type of berry. In some embodiments, a pomace can be from a plant including, but not limited to, apple, pomegranate, black currant, blueberry, cranberry, lingnonberry, cherry, grape, muscadine, blackberry, *aronia, Sorbaronia mitschurinii, Camellia* spp. (tea) (e.g., *Camellia sinensis, Camellia oleifera*), and/or peanut (*Arachis hypogaea*) (e.g., peanut skins).

In some embodiments, a fermented fruit product can be from a plant including, but not limited to, black currant, blueberry, cranberry, lingnonberry, cherry, grape, muscadine, blackberry, green tea (*Camellia* spp.), cinnamon, *aronia, Sorbaronia mitschurinii*, peanut skins, and/or any combination thereof.

In some embodiments, a protein product can be a soluble, semi-soluble or solid protein product. The protein product can include a flour. In some embodiments, a protein product can include, but is not limited to peanut, tree nut, milk, whey, egg, soy, fish, shellfish, rice, wheat, and/or any combination thereof. Non-limiting examples of a protein product may include whey protein isolate, peanut flour, egg albumin, soy protein isolate and defatted soy flour, wheat, barley or rye flour or protein isolates or gluten from wheat, barley or rye. In some embodiments, a tree nut can include, but is not limited to, walnut, almond, hazelnut, cashew, pistachio, or Brazil nut, or any combination thereof.

Methods of dehydration are well known in the art of food and supplement manufacturing. Thus, for example, in some embodiments, dehydrating can include, but is not limited to, freeze drying (e.g., lyophilizing), spray drying and/or vacuum tray drying. In some embodiments, dehydrating a protein-polyphenol aggregate matrix produces a dry granular aggregate.

Additionally provided herein are protein-polyphenol aggregate matrices produced by the methods of the invention described herein. In some embodiments, the concentration of polyphenols in a protein-polyphenol aggregate matrix can be in the range of about 1 percent to about 75 percent (w/w) of the weight of the total aggregate, optionally the concentration of polyphenols in a protein-polyphenol aggregate matrix can be about 1 percent to about 40 percent or at least about 15% the weight of the total aggregate. Accordingly, in some embodiments, the concentration of polyphenols in a protein-polyphenol aggregate matrix comprises, consists essentially of, or consists of about 1% to about 70%, about 1% to about 60%, about 1% to about 50%, about 1% to about 35%, about 1% to about 30%, 1% to about 25%, about 1% to about 20%, about 1% to about 15%, about 1% to about 10%, about 1% to about 5%, about 5% to about 70%, about 5% to about 60%, about 5% to about 50%, about 5% to about 40%, about 5% to about 35%, about 5% to about 30%, about 5% to about 25%, about 5% to about 20%, about 5% to about 15%, about 5% to about 10%, about 10% to about 70%, about 10% to about 60%, about 10% to about 50%, about 10% to about 40%, about 10% to about 35%, about 10% to about 30%, about 10% to about 25%, about 10% to about 20%, about 10% to about 15%, about 15% to about 70%, about 15% to about 60%, about 15% to about 50%, about 15% to about 40%, about 15% to about 35%, about 15% to about 30%, about 15% to about 25%, about 15% to about 20%, about 20% to about 70%, about 20% to about 60%, about 20% to about 50%, about 20% to about 40%, about 20 to about 35%, about 20 to about 30%, about 20% to about 25%, about 25% to about 40%, about 25% to about 35%, about 25% to about 30%, about 30% to about 70%, about 30% to about 60%, about 30% to about 50%, about 30 to about 40%, about 30 to about 35%, about 35% to about 40% (w/w), and the like, of the weight of the total aggregate. Thus, in some embodiments, the concentration of polyphenols in a protein-polyphenol aggregate matrix comprises, consists essentially of, consists of about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40% (w/w) of the weight of the total aggregate or any range or value therein. In representative embodiments, a protein-polyphenol aggregate matrix is provided that comprises, consists essentially of, or consists of about 1% to about 40% polyphenols (w/w).

Under oxidative conditions, at or near physiological pH and with or without enzymatic catalysis, phenols are readily transformed to quinones which may then interact irreversibly with nucleophilic groups (e.g., SH, NH2) on a protein molecule via covalent bonding. Furthermore, by increasing the ratio of polyphenols to proteins in the process of producing the protein-polyphenol aggregate matrix, the formation of irreversible bonds between the protein and polyphenols is favored. Because the low sugar or sugar free concentrated polyphenolic extract of the invention can be prepared as described herein to have a high polyphenolic content of at least about 30%, as described herein, a wide range of polyphenol to protein ratios can be achieved in the protein-polyphenol aggregate matrix. This in turn provides the ability to produce protein-polyphenol aggregate matrices having a wide range of covalent to non-covalent bonds between the protein and polyphenols and therefore a wide range of bond strengths in the protein-polyphenol aggregate matrices. Notably, for some immunotherapies (e.g., clinical desensitization procedures) a physician may desire a range of bond strengths present at different time points during a long term desensitization procedure. Further, for some functional foods, a manufacturer may want to absolutely ensure tight binding between the polyphenol and protein to reduce the possibilities of an allergenic epitope becoming exposed following digestion in the gut.

In some embodiments, a protein-polyphenol aggregate matrix may be an immunotherapeutic protein product comprising, consisting essentially of, or consisting of about 5% to about 75% (w/w) polyphenols. In some embodiments, the immunotherapeutic protein product may comprise, consist essentially of, or consist of about 5% to about 40% or 5% to 30% polyphenols (w/w). In further embodiments, the immunotherapeutic protein product may comprise, consist essentially of, or consists of at least about 30% polyphenols (w/w). 5% to about 70%, about 5% to about 60%, about 5% to about 50%, about 5% to about 40%, about 5% to about 35%, about 5% to about 30%, about 5% to about 25%, about 5% to about 20%, about 5% to about 15%, about 5% to about 10%, about 10% to about 75%, about 10% to about 70%, about 10% to about 60%, about 10% to about 50%, about 10% to about 40%, about 10% to about 35%, about 10% to about 30%, about 10% to about 25%, about 10% to about 20%, about 10% to about 15%, about 15% to about 75%, about 15% to about 70%, about 15% to about 60%, about 15% to about 50%, about 15% to about 40%, about 15% to about 35%, about 15% to about 30%, about 15% to about 25%, about 15% to about 20%, about 20% to about 75%, about 20% to about 70%, about 20% to about 60%, about 20% to about 50%, about 20% to about 40%, about 20 to about 35%, about 20 to about 30%, about 20% to about 25%, about 25% to about 75%, about 25% to about 70%, about 25% to about 60%, about 25% to about 50%, about 25% to about 40%, about 25% to about 35%, about 25% to about 30%, about 30% to about 75%, about 30% to about 70%, about 30% to about 60%, about 30% to about 50%, about 30 to about 40%, about 30 to about 35%, about 35% to about 40% (w/w), and the like. Thus, in some embodiments, the immunotherapeutic protein product comprises, consists essentially of, or consists of at least about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75 percent (w/w), or any value or range therein, of polyphenols. In representative embodiments, the immunotherapeutic protein product may comprise, consist essentially of, or consist of about 5% to about 40% polyphenols (w/w). Thus, in some embodiments, a protein-polyphenol aggregate matrix of the invention can comprise a highly concentrated polyphenol content such that the polyphenolic equivalent of about 5 to about 10 servings of fruit can be ingested in a small volume of protein-polyphenol aggregate matrix (e.g., about 20 g to about 30 g).

The present inventors have demonstrated that the protein-polyphenol aggregate matrices of the invention can comprise anti-diabetic activities, enhanced bioavailability, and functional food applications. The protein-polyphenol interactions achieved can be both reversible (non-covalent (hydrogen bonding, van der Waals forces)) and irreversible (covalent) bonds between the protein and phenolic substrate. Binding of polyphenols to allergens changes the protein structure and/or masks or alters IgE binding epitopes—rendering the proteins less allergenic.

Accordingly, in some embodiments, the invention provides a method of attenuating an allergic response in a subject in need thereof, comprising administering to the subject the protein-polyphenol aggregate matrix of the invention. In some embodiments, the protein-polyphenol aggregate matrix may be in any form effective for delivering an immunotherapeutic product. Non-limiting examples of the form in which protein-polyphenol aggregate matrix of the invention may be administered includes, for example, a powder, a gel, a gummy product, a chewable tablet or a gum, wherein the protein-polyphenol aggregate matrix comprises, consists essentially of, or consists of a concentration of polyphenols of, for example, about 5% to about 40% (w/w) polyphenol to protein.

As used herein "attenuating an allergic response" means reducing a subject's response to an allergen. A reduction in a subject's response to an allergen can be by about 1% to about 100%. Generally, a subject is first provided a small amount of the protein-polyphenol aggregate matrix, which amount is increased over time with the amount, time and duration of treatment being varied by the clinician for the subject being treated.

In some embodiments, a method of producing a food product having reduced reactivity of a protein component is provided, comprising adding the protein-polyphenol aggregate matrix of the invention to a composition for the production of the food product, thereby producing a food product having reduced reactivity. In some embodiments, the food product comprises, consists essentially of, or consists of about 0.1% to about 0.2% total phenolics. In some embodiments, the reactivity of a of a protein component of a food product may be reduced by about 10% to about 85% as compared to a protein component in a food product for which the protein-polyphenol aggregate matrix of the invention has not been added. In some embodiments, the reduced reactivity of the protein component increases foam stability in a food product. In some embodiments, increased foam stability means increased drainage time (rate of drainage) and increased yield stress of the foam.

In some embodiments, a method of producing a high protein bar having reduced hardening is provided, comprising adding the protein-polyphenol aggregate matrix of the invention to a composition for the production of the high protein bar, thereby producing a high protein bar having reduced hardening. In some embodiments, the high protein bar produced comprises about 0.1% to about 0.2% total phenolics. In some embodiment, wherein the high protein bar produced has a reduced hardening for a period from at least about two weeks to about six months (e.g., 2, 3, 4, 5, 6, 7, 8, 9, 10, 11, 12, 13, 14, 15, 16, 17, 18, 19, 20, 21, 22, 23, 24 weeks, or more) from time of production as compared to a high protein bar not made with the protein-polyphenol aggregate matrix.

As understood by those of ordinary skill in the art, high protein in a food product, e.g., a protein bar, can be about 25% to about 40% protein. In some embodiments, the protein-polyphenol aggregate matrix of the invention can comprise about 10% to about 100% of the protein in the food product (e.g., 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, 100% of total protein in the food product, and the like, and any range or value therein).

The invention will now be described with reference to the following examples. It should be appreciated that these examples are not intended to limit the scope of the claims to the invention, but are rather intended to be exemplary of certain embodiments. Any variations in the exemplified methods that occur to the skilled artisan are intended to fall within the scope of the invention.

EXAMPLES

In this process, edible proteins (soluble, semi-soluble, and/or insoluble proteins) are complexed with low sugar or sugar free polyphenolic extracts, then dehydrated together to produce dry granular protein-polyphenol chimeric aggregates (protein-polyphenol aggregate matrix). A feature of this process is that the polyphenol source can be stably loaded onto to protein carriers resulting in very high concentrations of polyphenol/g matrix (e.g., polyphenol complexed protein aggregate) as compared to art known methods). This novel strategy enhances irreversible (covalent) protein-polyphenol binding in the polyphenol-complexed protein. Per the methods of the invention, under oxidative conditions, phenols are readily transformed to quinones which may then interact irreversibly with nucleophilic groups (e.g. SH, NH2) on the protein molecule via covalent bonding.

Polyphenol-complexed protein aggregates produced in the processes of this invention can be more safely and effectively used in allergy therapies (e.g. oral immunotherapy or other desensitization strategies), and may enable development of food products that will not provoke adverse allergic reactions in sensitive individuals.

In contrast to the art known methods, the present invention provides methods for attenuating the allergenicity of semisolid and soluble proteins, such as egg, milk, and soy, in addition to solid proteins such as peanut.

Thus, the present invention provides novel hypoallergenic food proteins for use in desensitization therapies and hypoallergenic food ingredient formulation for sensitive individuals.

Example 1. Preparation of a Concentrated Polyphenol Extract

A series of complexed protein-polyphenol ingredients using whey protein isolate (WPI), egg protein (EP), defatted peanut flour (DPF), and soy protein isolate (SPI) were complexed with pomace extract/low sugar or sugar free polyphenol rich extracts (cranberry (CB), green tea (GT) blackcurrant (BC) and cinnamon (CN)), having concentrations of 30%, 40% and 50% total polyphenols (TP) after the complexation (sorption) process (e.g., the polyphenol may be absorbed in the protein, or adsorbed to the surface of the protein, or any combination thereof).

Pomaces are extracted with 50% ethanol solution (1:5 w/v) including heating for two hours. The extracts are filtered and ethanol is evaporated to produce an aqueous extract. It is noted that a low sugar or sugar free concentrated source of polyphenol can be achieved by (1) extracting from fruit pomaces (resulting in a naturally low or no sugar extract); 2) extracting from a polyphenol rich plant source that typically doesn't have free sugars including but not limited to green tea or cinnamon, 3) fermenting a fruit juice source to eliminate sugars and/or 4) use of a resin (e.g., AMBERLITE® or a C18 column), in order to remove sugars from an extract.

Thus, when so desired, a polyphenol extract may be further concentrated and excess sugars removed by mixing aqueous extract with an ion exchange resin such as, for example, AMBERLITE® or DIAION® HP 50, with stirring for about 20 min. The resin can then be washed with water several times (about 10× of resin volume), and then polyphenols eluted with ethanol. The ethanol elute is evaporated using a rotavapor and freeze-dried to afford the polyphenol-rich fraction. Total phenolic (TP) and proanthocyandin content is measured using Folin Ciocalteau and DMAC assays, respectively.

Example 2. Preparation of the Polyphenol-Complexed Protein

A polyphenol rich fraction from Example 1 was dissolved in water and is added to the protein source at different levels (1 L extract to 200, 100, or 50 g protein), the pH is adjusted to 4 and the mixture is lyophilized. The same procedure can be performed after the addition of polyphenol oxidase enzyme (tyrosinase enzyme), allowing the enzymatic reaction to take place for 10, 20 and 60 min, before dehydration.

Dehydration of the complexes to dry granular aggregates is accomplished by methods including but not limited to lyophilization, or vacuum tray or spray drying tactics. The physico-chemical (water activity, particle size) and phytochemical properties of the protein-polyphenol matrices are determined with treatments normalized based on protein content. The complexed protein-polyphenol matrices (prepared from whey, egg, peanut and soy proteins) are gauged to determine suppression of antigen-mediated mast cell degranulation and pro-inflammatory cytokine synthesis in culture murine and human cells.

The most promising matrices from in vitro trials are selected and investigated for whether the protein-polyphenol complex influences clinical anaphylactic responses in sensitized animals (this could be performed first in a passive systemic anaphylaxis model, then in a food sensitivity model.

Example 3. Results and Discussion

Prior to the methods of the invention described herein, the total amount of polyphenols that could be captured in a polyphenol-protein product was limited due to, for example, the complexation and centrifugation steps. A feature of the novel technology of the invention as described herein is that the protein product can be loaded with polyphenol without such a constraint. Therefore, the total amount of complexed polyphenolics held by the protein product (the total polyphenol concentration) can be levels of magnitude higher than that achievable using art known methods.

As seen in FIG. 1, the new technology of co-dehydration of complexed protein-polyphenol aggregates (first bar) results in a much higher mg/g total phenolics calculated as gallic acid equivalent (TP, GAE) compared to the aggregates produced using HPI or SPI, in the adjacent bars.

The concentration of phenolics that complex with the protein can be increased several times using the methods described herein by manipulating the ratios of protein to the polyphenol source (w/v), while the art known methods do not allow higher values of polyphenol complexation with protein due to, for example, the presence of high concentration of sugar in the polyphenol extracts made from juices that interfere with the process and the overall limited amount of polyphenols that can be sorbed to the protein. In contrast, the amount of polyphenol that can be sorbed to the protein using the methods of the present invention is limitless.

Using the novel methods described herein, we have produced blueberry polyphenol-complexed protein aggregates delivering 70-75 mg/g polyphenols using blueberry pomaces as the source of polyphenols. Three to 3.5 g of this aggregate (equivalent to one serving (75 g) of fresh blueberries) is added to a serving size (46 g) of a shelf stable yogurt based spread.

Figure 2:
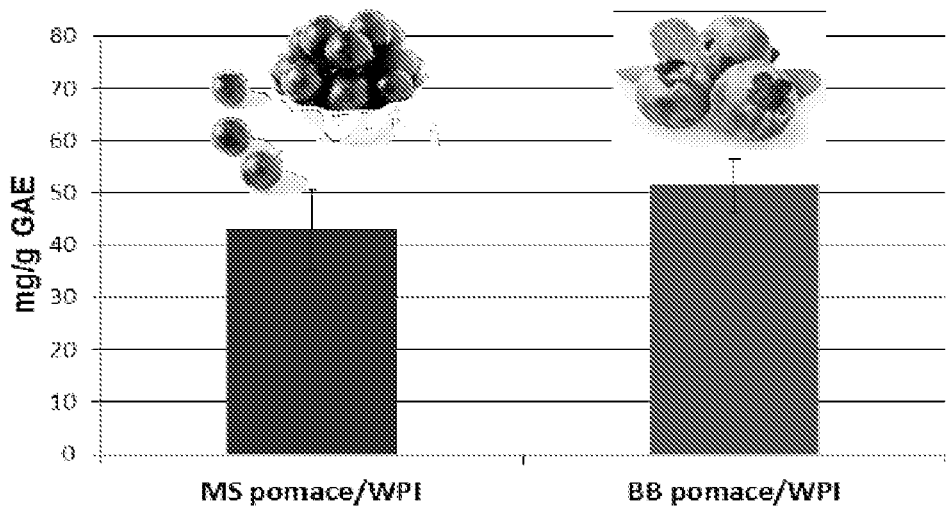
FIG. 2 shows whey protein isolate (WPI) complexed with muscadine (MS) pomace extract or blueberry (BB) pomace extract using the methods of the invention described herein.

FIG. 2 shows high concentrations of polyphenols captured from muscadine and blueberry pomaces and complexed into protein-polyphenol aggregate matrix using the methods of the present invention. Thus, the concentration of phenolics complexed with the protein can be increased several times by using a polyphenol-rich fraction prepared from a pomace extract prepared using the methods of the invention as described herein The methods of invention described herein can be food grade. The allergenic epitopes of the edible proteins are masked and/or changed in conformation to blunt allergenicity using the methods described herein, allowing desensitization to the protein without provoking allergy symptoms. Fruit waste materials (pomaces), which consist of the skins/seeds/fibers after the juicing process, are a ready and economical source of polyphenols. In the pomaces, the sugar has been removed/extracted with the juice and further the pomace is a substantially less expensive polyphenol donor tissue than whole fruit or fruit juice. The technology has applications in allergy therapy, and in future development of hypoallergenic food products.

Example 4. Attenuation of Allergenicity Via Formation of Stable Protein-Polyphenol Aggregate Particles Methods for Production of Protein-Polyphenol Aggregate Particle with Attenuated Allergenicity A. Plant and Protein Materials Used—

Commercially available whey protein isolate (Davisco, Le Sueur, Minn., USA) and egg white protein (Sigma-Aldrich, St. Louis, Mo., USA) were used as food protein sources. Commercially available organic green tea leaves (QTrade Teas & Herbs, Cerritos, Calif., USA), cranberry pomace (Ocean Spray, Lakeville-Middleboro, Mass., USA), lowbush blueberry pomace (Jasper Wyman & Son, Cherryfield, Me., USA), cinnamon stick powder (Frontier Co-op, Norway, Iowa, USA), and an anthocyanin- and proanthocyanidin-enriched blackcurrant extract powder (Just the Berries, Los Angeles, Calif., USA) were used as polyphenol sources.

B. Preparation of Plant or Pomace Extracts—

Green tea leaves, cranberry pomace and blueberry pomace were kept at −80° C. until use. Cranberry and blueberry pomace were freeze-dried prior to extraction to remove residual moisture. Dry green tea leaves and pomaces were ground into a fine powder for extraction. Ground green tea leaves and blueberry pomace were mixed with 50% aqueous ethanol at a ratio of 1:5 (w/v) while cinnamon stick powder and cranberry pomace were mixed at a ratio of 1:10 (w/v) to ensure full hydration. Each mixture was then incubated for 2 h at 80° C. in a water bath. Following incubation, each mixture was allowed to equilibrate for several minutes to room temperature, was subsequently filtered using cheese cloth (separation of insoluble plant material), and the ethanol was evaporated from each sample using a Rotavap system (Buchi, Switzerland). Each extract was then centrifuged and filtered a few times and the evaporated ethanol fraction was reconstituted with deionized water. Each solution was centrifuged one more time to separate remaining insoluble plant material. The final crude aqueous extracts were stored at −20° C. until further analyses or complexation with food proteins. The blackcurrant extract was reconstituted in deionized water and stored at −20° C. also until further use.

C. Preparation of Protein-Polyphenol Aggregate Particles—

Total phenolic content in extracts (prior to complexation with proteins) was determined. The concentration of total polyphenolic compounds was determined using the Folin-Ciocalteu assay (Herald et al., 2012). Results were expressed as mg mL$^{-1}$ gallic acid equivalents (GAE) based on a gallic acid standard curve. The amount of extract (mL) and protein (g) required to generate dry, stable protein-polyphenol aggregate particles containing 5, 10, 15, 30, or 40% total polyphenol content after complexation was added together and mixed under constant agitation for 15 min at room temperature. The protein was allowed to fully blend in with the extract prior to the agitation time. When protein:polyphenolic extract ratios were too high, the extract was diluted to a total volume of approximately 100 mL with deionized water to ensure proper mixing. Once proteins were mixed with aqueous crude plant or berry extracts, each sample was frozen and subsequently freeze-dried to afford the dry, stable protein-polyphenol aggregate particles.

D. Total and Individual Proanthocyanidin Content in Plant and Berry Extracts —

Total and individual proanthocyanidin contents were determined by means of normal phase High Performance Liquid Chromatography (HPLC)-fluorescence analysis. An Agilent 1200 HPLC system with a fluorescence detector (FLD) and photodiode array detector (DAD) was used (Agilent Technologies, Englewood, Colo., USA). The column used was a Develosil Diol column, 250 mm×4.6 mm×5 µm (Phenomenex, Torrance, Calif., USA) and the mobile phase was composed of (A) acetonitrile:acetic acid (98:2, v/v) and (B) methanol:water:acetic acid (95:3:2, v/v/v). A linear gradient was used for compound separation with a flow rate of 0.8 mL min$^{-1}$: 0-35 min, 0-40% B; 35-40 min, 40-100% B; isocratic 100% B, 45 min; 100-0% B, 50 min; and 0% B to 55 min (Wallace and Gusti, 2010). Quantification of compounds was performed using peak areas and external calibration curves (monomer (DP1) through tetramer (DP4) commercial standards). PAC with DP>4 including polymers were expressed as DP4 equivalents.

E. Identification of Phenolic Compounds in Plant and Berry Extracts—

LC-MS-IT-TOF (Liquid Chromatography-Ion Trap-Time of Flight-Mass Spectrometry) was used to separate and identify phenolic compounds in plant and berry extracts. A Shimadzu LC-MS-IT-TOF instrument equipped with a Prominence HPLC system was used. The separation of compounds in the HPLC was performed using a Shim-pack XR-ODS column (50 mm×3.0 mm×2.2 µm) with a constant column temperature of 40° C. The binary solvent system consisted of 0.1% formic acid in water (A) and methanol (B). Compounds were eluted into the ion source (electron spray ionization, ESI) at a flow rate of 0.35 mL min$^{-1}$ with a step gradient of 5-60% B over 40 min, isocratic at 60% B over 2 min, and returned to 5% B over 2 min. Ionization was conducted in the negative and positive mode and compounds of interest determined in the negative mode (Grace et al., 2013). Compounds were identified by their MS, MS/MS spectra, and HPLC retention times and by comparison with the literature.

F. Sodium Dodecyl Polyacrylamide Gel Electrophoresis (SDS-PAGE) and Immunoblotting—

SDS-PAGE was used to observe protein distribution in protein-polyphenol aggregate particles and unmodified protein powders. The amount of protein-polyphenol aggregate particles or unmodified protein required to provide equivalent protein content (2 mg) was used. One milliliter dispersions in Laemmli SDS sample loading buffer (2×) (BioRad, Hercules, Calif., USA) were prepared and mixed thoroughly. Five microliters of each dispersion were subsequently added to 5 µL Laemmli SDS sample loading buffer (2×) containing 5% β-mercaptoethanol (BioRad, Hercules, Calif., USA) resulting in 10 µg protein in 10 µL. Samples were mixed and incubated for 5 min at 95° C. and subsequently loaded onto a gel (4-20% mini-PROTEAN TGX precast gel, BioRad, Hercules, Calif., USA). The gel was run for 40 min at 200 V, stained with Coomassie Blue G-250 stain (BioRad, Hercules, Calif., USA) and destained overnight in deionized water.

For immunoblotting (Western blotting) proteins in whey protein-blueberry polyphenol aggregate particles or unmodified whey proteins were transferred onto a PVDF (Polyvinylidene fluoride) membrane (Life Technologies, Grand Island, N.Y., USA) via electroblotting following separation by SDS-PAGE. Immunoblotting was performed using pooled human plasma from eight milk-allergic individuals obtained from PlasmaLab International (Everett, Wash., USA). The blot was ultimately treated with a chemiluminescence substrate and developed on a ChemiDoc MP system equipped with a CCD camera (BioRad, Hercules, Calif., USA). Milk-specific IgE levels in the pooled plasma ranged from 7.04 to >100 kU L$^{-1}$ as determined via ImmunoCAP (Phadia, Uppsula, Sweden).

G. Nitroblue Tetrazolium (NBT) Staining—

Nitroblue tetrazolium can be used to detect covalent bonds in protein-polyphenol aggregates on nitrocellulose or PVDF membranes after electroblotting (colorimetric assay). At an alkaline pH, the catechol moiety (of the polyphenol) catalyzes redox cycling in the presence of glycine, generating superoxide that reduces NBT to the insoluble formazan (blue-purple color). Proteins specifically stained by NBT indicate covalent bonds between oxidized polyphenols (quinones) and proteins (Brudzynski et al., 2013; Ishii et al., 2008). Here, after electroblotting, the dry PVDF membrane was briefly rehydrated in 100% methanol and subsequently incubated with NBT (Sigma-Aldrich, St. Louis, Mo., USA) in potassium glycinate buffer (pH 10) for 45 min at room temperature with constant agitation in the dark (Paz et al., 1991). The membrane was then briefly washed twice with a sodium borate solution and soaked in fresh sodium borate solution overnight at room temperature. The PVDF membrane was washed in deionized water and photographed while still wet.

Results for Protein-Polyphenol Aggregate Particles with Attenuated Allergenicity A. Phytochemical Analyses of Polyphenol-Donor Plant Material (Extracts)—

The highest concentration of total phenols was found in the green tea leaves extract (36.76 mg mL$^{-1}$), followed by the blackcurrant extract (34.18 mg mL$^{-1}$). (Note that this blackcurrant extract was obtained commercially as a highly concentrated, sugar free extract, therefore as expected had a much higher polyphenol concentration than blueberry or cranberry pomace extracts). The least amount was determined in cranberry pomace extract (0.83 mg mL$^{-1}$) (Table 1). The highest concentration of total procyanidins was found in blackcurrant and green tea leaves extracts, 2.29 mg mL$^{-1}$ and 2.55 mg mL$^{-1}$, respectively, whereas the cranberry pomace extract had the least amount of procyanidins (0.47 mg mL$^{-1}$). Green tea leaves extract was rich in monomers and dimers (1.33 mg mL$^{-1}$ and 0.55 mg mL$^{-1}$, respectively) while blackcurrant and blueberry pomace extract were particularly rich in polymers (0.66 mg mL$^{-1}$ and 0.60 mg mL$^{-1}$, respectively) (Table 2). LC-MS analysis confirmed that green tea mainly contains monomeric (e.g. catechin) and dimeric (e.g. epigallocatechin-epigallocatechin gallate) procyanidins (Table 3). Although results obtained by HPLC showed that the blackcurrant extract contained procyanidins with various degrees of polymerization, by LC-MS, only a procyanidin dimer and trimer were structurally characterized. Both cinnamon stick powder extract and cranberry pomace extract were comprised of procyanidin dimers, trimers, tetramers and pentamers (Table 3). On the other hand, monomers, dimers, trimers and tetramers were identified in the blueberry pomace extract. MS spectra will need to be further analyzed in order to fully identify procyanidins that were recorded on the HPLC chromatogram.

B. Protein Distribution, IgE Binding Capacity and Nitroblue Tetrazolium Staining—

Figure 3:
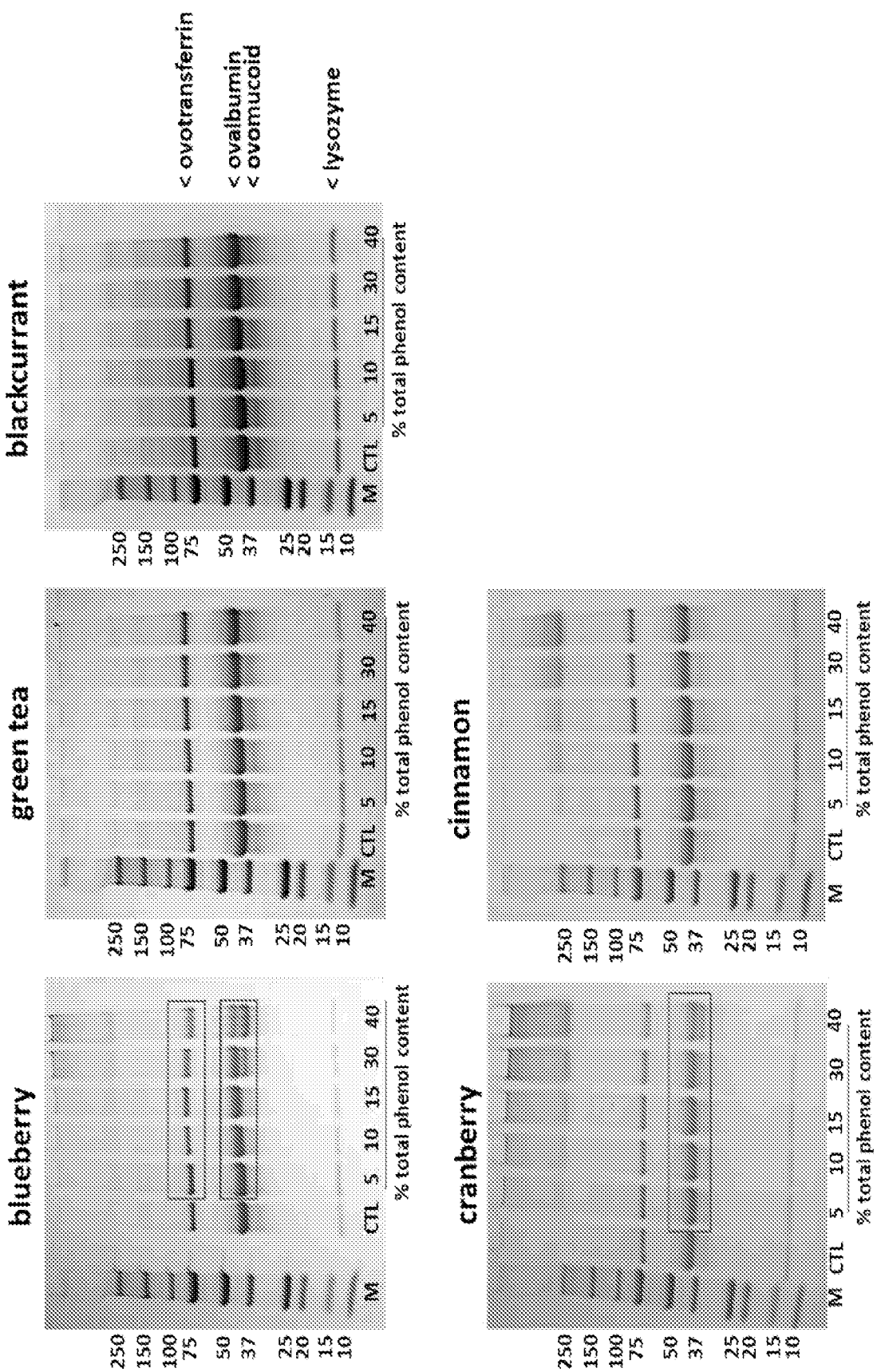
FIG. 3 shows separation of egg white proteins in unmodified egg white protein or egg white protein-polyphenol aggregate particles containing 5, 10, 15, 30, and 40% total phenols. M, molecular weight marker (kDa); CTL, control (unmodified egg white proteins). Approximate locations for egg white allergens are indicated. Boxes highlight changes in protein profiles and electrophoretic mobility with an increase of % total phenol content. Gray scale was used and contrast was adjusted to improve visualization.
Figure 4:
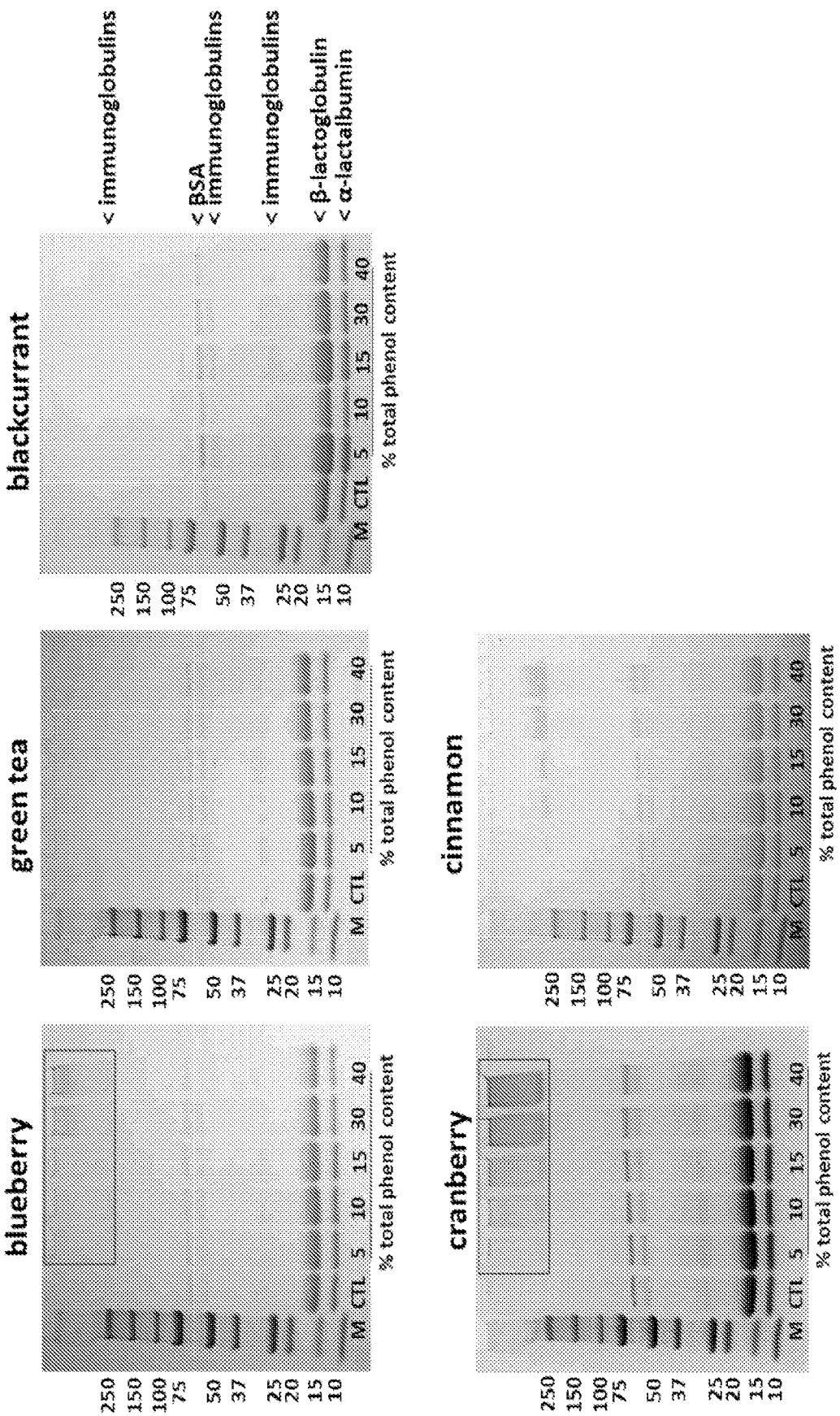
FIG. 4 shows separation of whey proteins in unmodified whey protein isolate or whey protein isolate-polyphenol aggregate particles containing 5, 10, 15, 30, and 40% total phenols. M, molecular weight marker (kDa); CTL, control (unmodified whey proteins); BSA, bovine serum albumin Approximate locations for whey allergens are indicated. Boxes highlight poorly resolved high molecular weight protein-polyphenol aggregate particles. Gray scale was used and contrast was adjusted to improve visualization.

Major whey or egg white proteins from both protein-polyphenol aggregate particles and unmodified protein powder were separated and identified by SDS-PAGE (FIG. 3 and FIG. 4). However, for egg white protein, complexation with blueberry or cranberry polyphenols resulted in changes of protein pattern and electrophoretic mobility and these effects appeared to be polyphenol dose dependent (FIG. 3, top panel boxes). For example, complexation of the egg white protein ovotransferrin (about 77 kDa) with increasing concentrations of blueberry polyphenols resulted in changes of electrophoretic mobility (protein band appears above or below about 77 kDa). This indicates that the molecular size and/or charge of ovotransferrin (egg protein) was modified through the complexation with blueberry polyphenols. Interestingly, although the egg white protein ovomucoid (about 28 kDa) was only visible in the control lane (CTL, unmodified egg white proteins), a protein band with slightly higher molecular weight than ovomucoid was observed in the 30 and 40% total polyphenol samples. Similar results were observed for the egg protein-cranberry polyphenol aggregate particles (FIG. 3, bottom panel box). Blueberry and cranberry pomace extracts share several of the same procyanidins (Table 3), which raises the question if the same procyanidins from either polyphenol source were bound to egg white proteins resulting in the SDS-PAGE data obtained. Future studies addressing what type(s) of polyphenols show the highest affinity for proteins tested will throw some light on this matter.

Changes in protein electrophoretic mobility/size, however, were not seen when whey protein isolate was used for complexation with polyphenol sources (FIG. 4). Alternatively, high molecular weight protein smears and material that did not enter the gel were observed particularly in the blueberry, cranberry and cinnamon samples but not in the control samples (FIG. 4, boxes top and lower panel), as was also noted for egg white protein (FIG. 3). Diffuse protein bands and band smearing suggest that proteins have been modified by polyphenols (Sampath et al., 1990; Alvarez, 2010).

Figure 5:
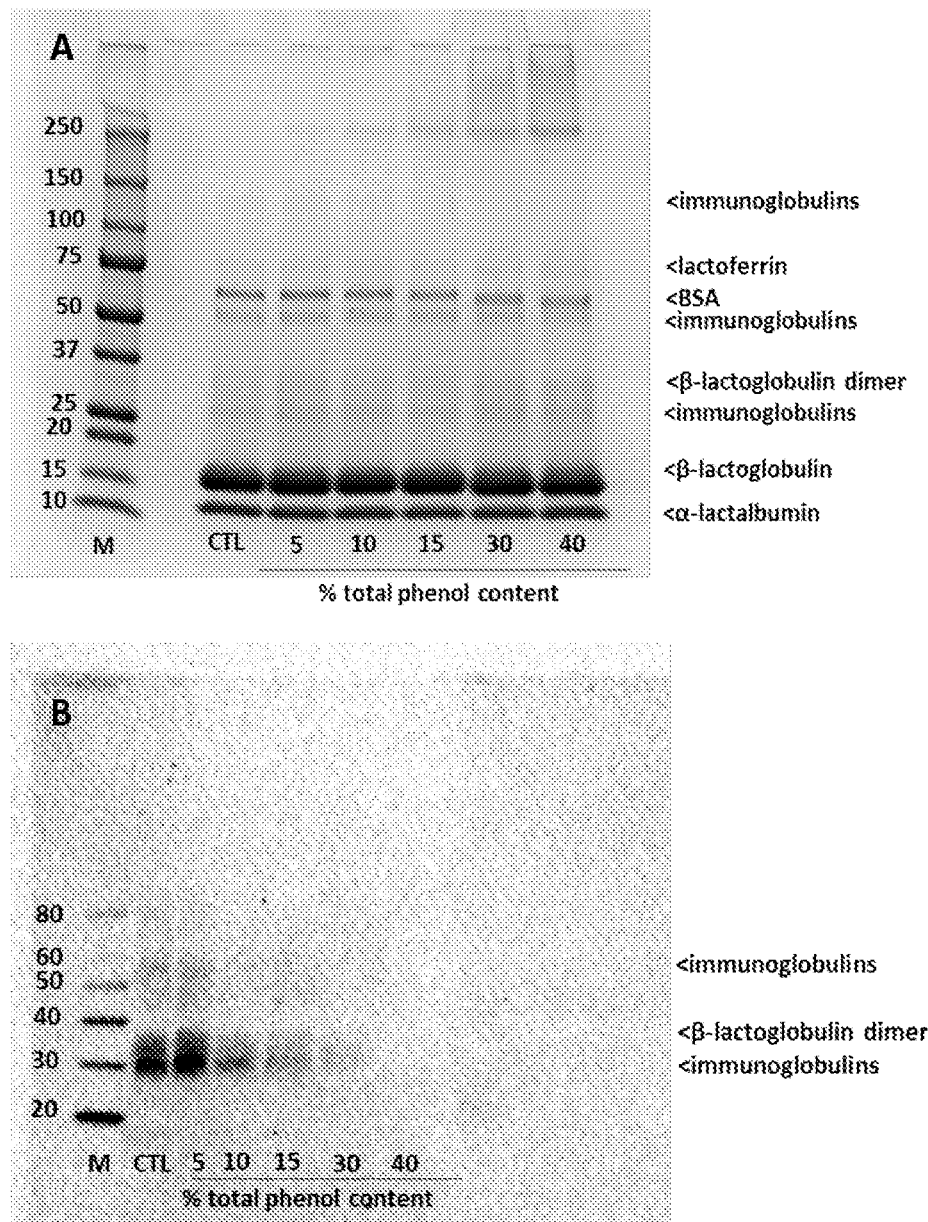
FIGS. 5A-5B show SDS-PAGE (FIG. 5A) and corresponding Western blot (FIG. 5B) of unmodified whey protein isolate and whey protein isolate-blueberry pomace polyphenol aggregate particles containing 5, 10, 15, 30, and 40% total phenols. M, molecular weight marker (kDa); CTL, control (unmodified whey proteins); BSA, bovine serum albumin. Whey allergens were tentatively identified and approximate locations are indicated.

Not all proteins that were separated by SDS-PAGE (FIG. 5A, a representative SDS-PAGE gel for whey protein-blueberry polyphenol aggregate particles) were recognized by IgE antibodies from pooled human plasma of milk-allergic individuals (FIG. 5B). Results suggest that the plasma recognized bovine immunoglobulins as well as β-lactoglobulin dimers (FIG. 5B). For those proteins, results showed that the complexation of proteins with polyphenols from blueberry pomace resulted in decreased IgE-binding capacity, and this was polyphenol concentration dependent. No IgE binding was observed to proteins in whey protein isolate-blueberry polyphenol aggregate particles containing 40% total polyphenols. Changes in IgE binding behavior and pattern compared to unmodified whey proteins could be attributed to polyphenol interference with whey protein-specific IgE binding.

Figure 6:
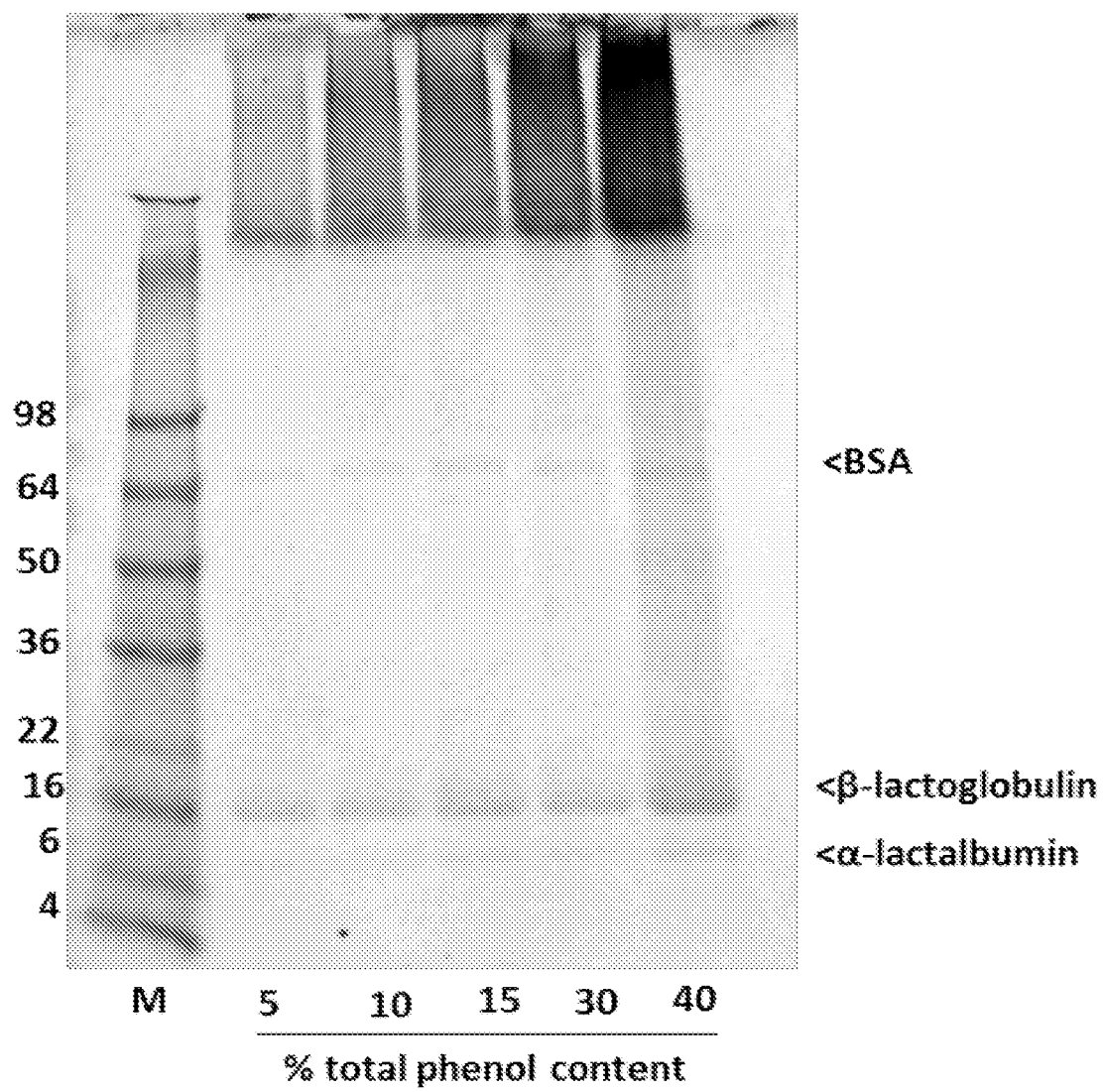
FIG. 6 shows redox-cycling staining of blueberry phenol-bound whey proteins by NBT (nitroblue tetrazolium) following SDS-PAGE and subsequent electrophoretic transfer to a polyvinylidene fluoride (PVDF) membrane. Approximate locations for whey proteins are indicated. M, molecular weight marker (kDa). Grey scale was used for the blot.

When electroblotted proteins were stained with NBT, poorly resolved high molecular weight protein-polyphenol aggregate particles with low electrophoretic mobility (FIG. 6, top) were clearly recognized, which could also be observed on respective SDS-PAGE (FIG. 4 and FIG. 5A). In addition, results suggest that particularly the whey proteins BSA (bovine serum albumin), β-lactoglobulin and α-lactalbumin were covalently modified by quinones (FIG. 6).

In general, polyphenols can interact with proteins either non-covalently (i.e. hydrogen bonds, hydrophobic effect) and/or covalently (covalent bonds), which are considered reversible or non-reversible interactions, respectively (Charlton et al., 2002; Siebert, 1999; Haslam, 1996). Our previous work with peanut allergens suggested that peanut protein-polyphenol interactions were partially hydrophobic (e.g. non-covalent) in nature (Plundrich et al., 2015). Results obtained for whey protein-blueberry polyphenol aggregate particles suggest that covalent bonds are also involved. Additional studies are required to evaluate the type(s) of interactions between food proteins (allergens) and polyphenols, which might not only be protein but also polyphenol source and concentration-dependent. Further studies are required to investigate correlations between type(s) of protein-polyphenol interactions as well as type(s) of polyphenols complexed and resulting outcomes in allergenic potential of the protein-polyphenol aggregate particles in vitro and in vivo.

In sum, certain combinations of food protein and polyphenol sources resulted in an altered protein distribution/mobility profile and it was shown that not all resolved (present) proteins after SDS-PAGE were recognized by milk-allergic patient plasma when unmodified whey proteins or whey protein-blueberry polyphenol aggregate particles were screened for IgE binding capacity. Furthermore, the IgE binding capacity for detectable whey allergens decreased with an increase of blueberry pomace polyphenol content in particles (dose-dependent manner) suggesting that IgE binding sites (epitopes) on whey allergens were modified or masked by blueberry polyphenols. This indicates that whey protein-blueberry polyphenol aggregate particles can be hypoallergenic in vivo.

Example 5. Chimeric Edible Protein-Polyphenol Aggregate Particles to Enhance Food Product Structure (Ingredient Functionality)

Methods for the Production of Protein-Polyphenol Aggregate Particles for Enhanced Food Product Structure/Functionality A. Preparation of Protein-Polyphenol Aggregate Particles—

Protein-polyphenol aggregate particles were formed by thoroughly mixing whey protein and powdered concentrated blackcurrant extract in deionized water, then spray-drying with a BÜCHI B-290 mini spray dryer (BÜCHI Labortechnik AG, Flawil, Switzerland) at an inlet temperature of 190° C.±5° C. and an outlet temperature of 90° C.±5° C. (100% aspiration and 40° spray angle). Provon® 190 whey protein isolate was sourced from Glanbia Nutritionals (90.17% protein, Twin Falls, Id., USA) and blackcurrant polyphenol powder from Just the Berries PD Corporation (96% total phenolics, Los Angeles, Calif., USA). The protein concentration of the powders was determined from nitrogen content measured using an Elementar Vario Cube Macro (Mt. Laural, N.J., USA) where a nitrogen to protein conversion ratio of 6.38 was used and found to be 88.58% for 1% protein-polyphenol powder and 83.39% for 5% protein-polyphenol powder.

B. Dispersibility of Protein-Polyphenol Aggregate Particles—

Dispersions of whey protein isolate, 1% polyphenol-protein, or 5% polyphenol-protein were prepared at 10% w/w protein stirred for 4 h in deionized water and pH adjusted using 1 M HCl or 1M NaOH. Dispersibility was determined from pH 3-7 and calculated as the amount of protein in the supernatant after centrifugation at 17,200×g at 15° C. (The protein content of the dispersions and resulting supernatant was measured before centrifugation).

C. Stability of Foams Prepared with Protein-Polyphenol Aggregate Particles —

Solutions of 10% w/w protein were prepared with whey protein isolate, 1% polyphenol-protein, or 5% polyphenol-protein by stirring in deionized water for 4 h adjusting pH to 7 using 1 M NaOH. Foams were formed by whipping 200 g of a protein solution for 20 min in a Kitchen Aid Mixer (St. Joseph's, MI, USA) at speed 8. Drainage ½ life is an indicator of foam stability and yield stress reflects the strength of a foam. Drainage ½ life was measured as the time for half the initial volume of the foam to drain. The yield stress was evaluated using a Brookfield model DV-I 25×LVTDV digital viscometer (Brookfield Engineering Laboratories Inc., Stoughton, Mass., USA) and a four-blade vane (1.0 cm in diameter and 2.4 cm high) set at 0.3 rpm. The torque reading was used to calculate yield stress ($\tau$) as follows, where $M_0$ is the maximum torque response, h is the height of the vane, and d is the diameter of the vane.

$$\tau = \frac{M_o}{\left[\left(\frac{h}{d}\right) + \frac{1}{9}\right]\left(\frac{\pi d^3}{2}\right)}$$

D. Use of Protein-Polyphenol Aggregate Particles as Ingredients to Inhibit Bar Hardening—

Bar hardening is an adverse effect that occurs in high-protein density formulations and which significantly reduces the shelf life and stability. Bar hardening is dependent on the ingredients use to form the bar, in particular the protein source used and its functionality. In these experiments, whey protein-cranberry polyphenol (WP-CP) particles were formed by adding 200 g of whey protein isolate (Provon 190, Glanbia Nutritionals, Twin Falls, Id., USA) to 1 L of cranberry juice with 50.2° Brix and 5.2 mg/ml TP gifted by Ocean Spray (Lakeville-Middleboro, Mass., USA), at either a dilution resulting in 2.5 mg/ml or 0.75 mg/ml total phenolics (TP) juice, during continuous stirring. After mixing for 4 hrs, particles were pelleted (7,000×g for 40 min.), re-suspended at 0.01 g/mL, and spray dried. The TP of the powders were evaluated using the Folin-Ciocalteu method and determined to be 0.1% and 2% TP for the two powders produced with two juice dilutions (Singleton et al., 1999)

Bars were made at 25:25:50 wt:wt ratio of vegetable oil:protein:corn syrup. Bars were formed using either WP-CP particles contain 0.1 or 0.2% TP or unmodified WPI. Bars were wrapped in parchment paper and rolled out to a 2.5 mm height, vacuum sealed. Storage was executed according to that of Li et al (2008) at 32° C. and about 55% humidity where 3.5 days equated to 1 week at room temperature. Textural properties were assessed using transient creep-recovery testing which measured the maximum compliance ($J_{max}$, indicating bar firmness) and percent creep-recovery (bar viscoelasticity). Tests were compete on a Stress Tech controlled-stress rheometer (ATS, Rheosystems, Bordentown, N.J., USA) with a 20 mm serrated plate and plate set up. Measurements were taken at a gap height of 2 mm at 25° C. Samples were exposed to a stress of 1 kPa for 20 s and allowed to recover for 200 s.

Results for Protein-Polyphenol Aggregate Particles in Food Product Structure Modulation A. Dispersibility of Protein-Polyphenol Aggregate Particles—

Figure 7:
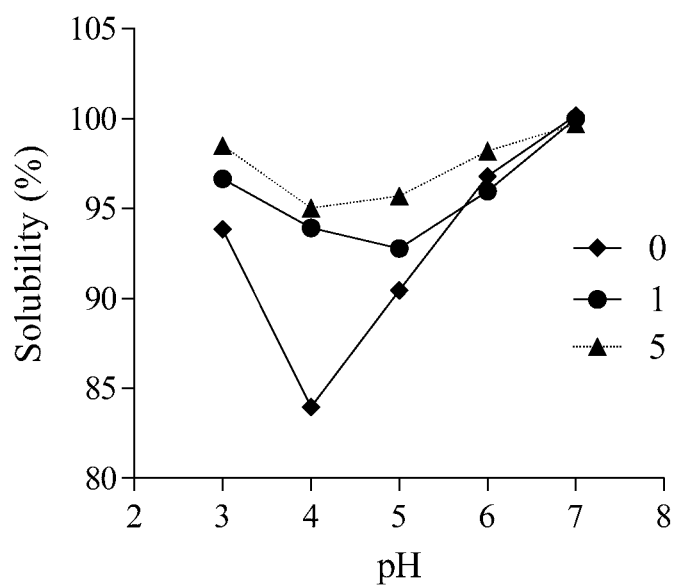
FIG. 7 shows protein dispersibility of protein powders containing 0, 1, or 5% total phenolics in 10% protein solutions across pH.

The dispersibility of the protein powders containing 1% and 5% phenolics remained more soluble than the control protein powder containing no phenolics at pHs 4 and 5 (FIG. 7). This suggests potential for incorporation in beverages with equal or greater dispersibility of protein.

B. Stability of Foams Prepared with Protein-Polyphenol Aggregate Particles —

Figure 8A:
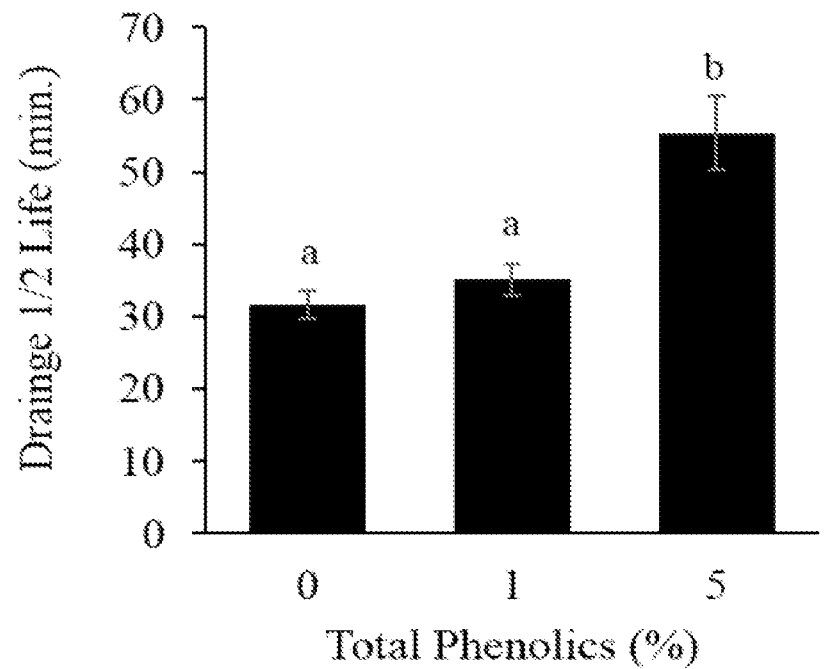
FIGS. 8A-8B show foaming properties, FIG. 8A drainage ½ life and FIG. 8B yield stress, of whey protein-polyphenol aggregates made with varying total phenolic contents. Different letters indicate values that are significantly different (p<0.01).
Figure 8B:
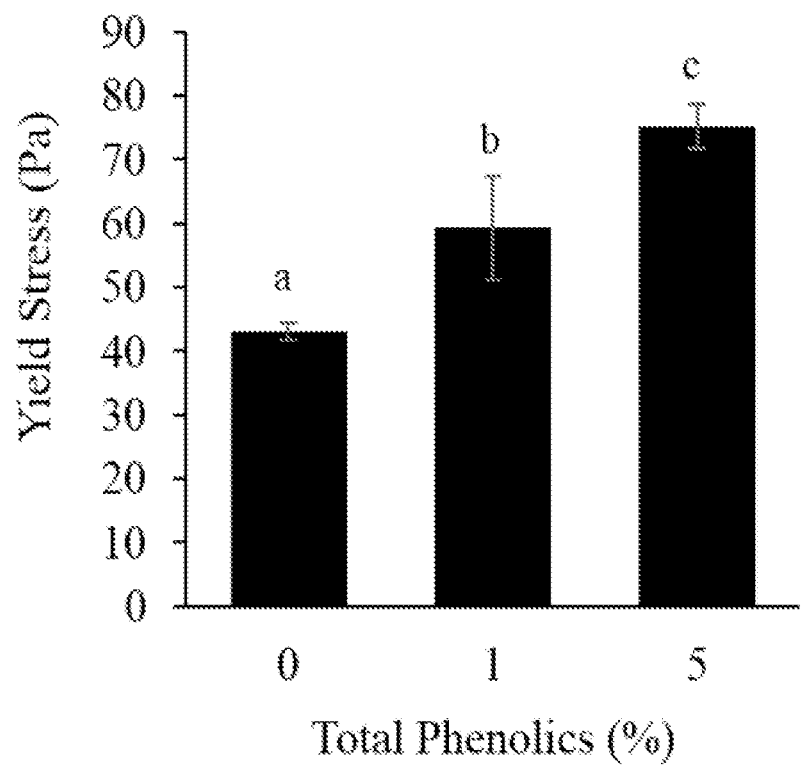

Foams prepared with protein-polyphenol aggregates which contained 1% polyphenols drained at the same rate of the control (polyphenol-free) foams. However, foams prepared using protein-polyphenol aggregate particles containing 5% polyphenols were more stable, as indicated by the increase in drainage time (FIG. 8). The yield stress of foams increased with increasing polyphenol content, suggesting that polyphenols are acting to strengthen/stabilize the foam (FIG. 8). The drainage ½ life is an indication of how long the foam will maintain bulk, before draining. Therefore, drainage ½ life is strictly related to the viscosity and density of the liquid surrounding the foam bubbles. The yield stress of a foam can be thought of as the "stiffness of peaks" and is dependent on solution viscosity, bubble size distribution, and interfacial tension. Considering factors that affect both drainage ½ life and yield stress, this suggests that the polyphenol-protein solutions could be more viscous, due to cross-linking of proteins via polyphenols, and more surface active than whey protein isolate alone. Increased viscosity and surface activity slows drainage and inhibits the breaking of bubbles.

C. Use of Protein-Polyphenol Aggregate Particles as Ingredients to Inhibit Bar Hardening—

Figure 9:
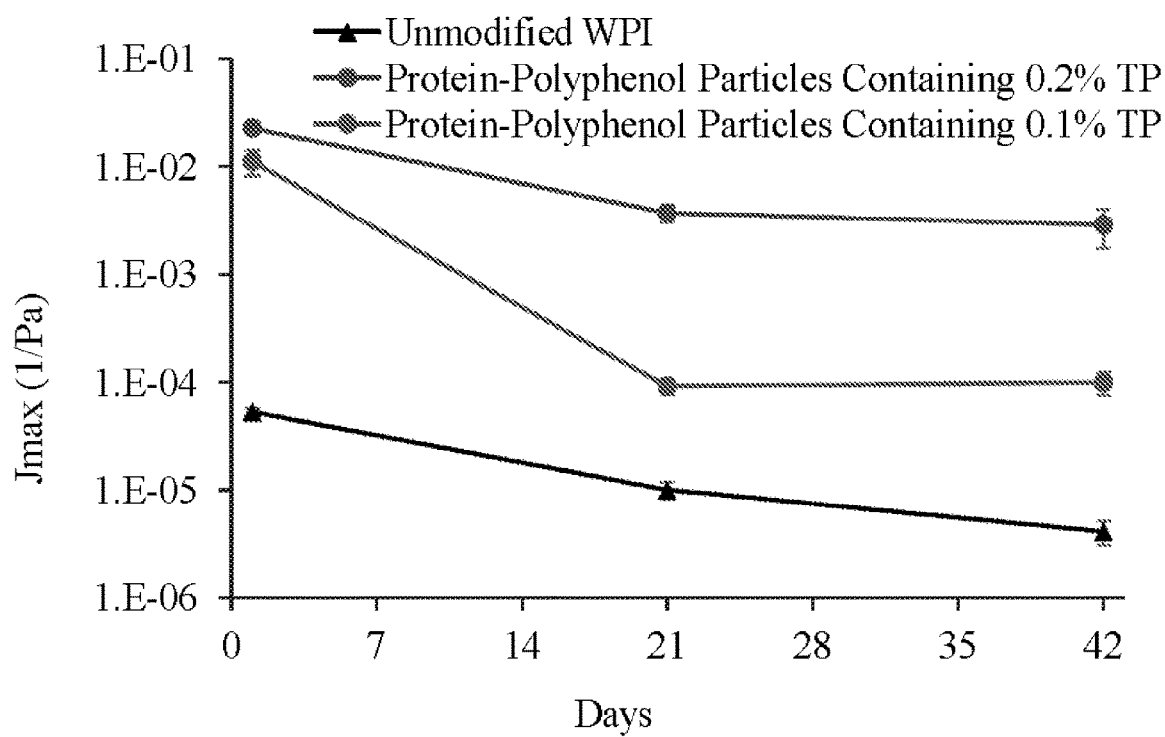
FIG. 9 shows maximum compliance of whey protein-polyphenol aggregates containing various amounts of total polyphenols (TP).
Figure 10:
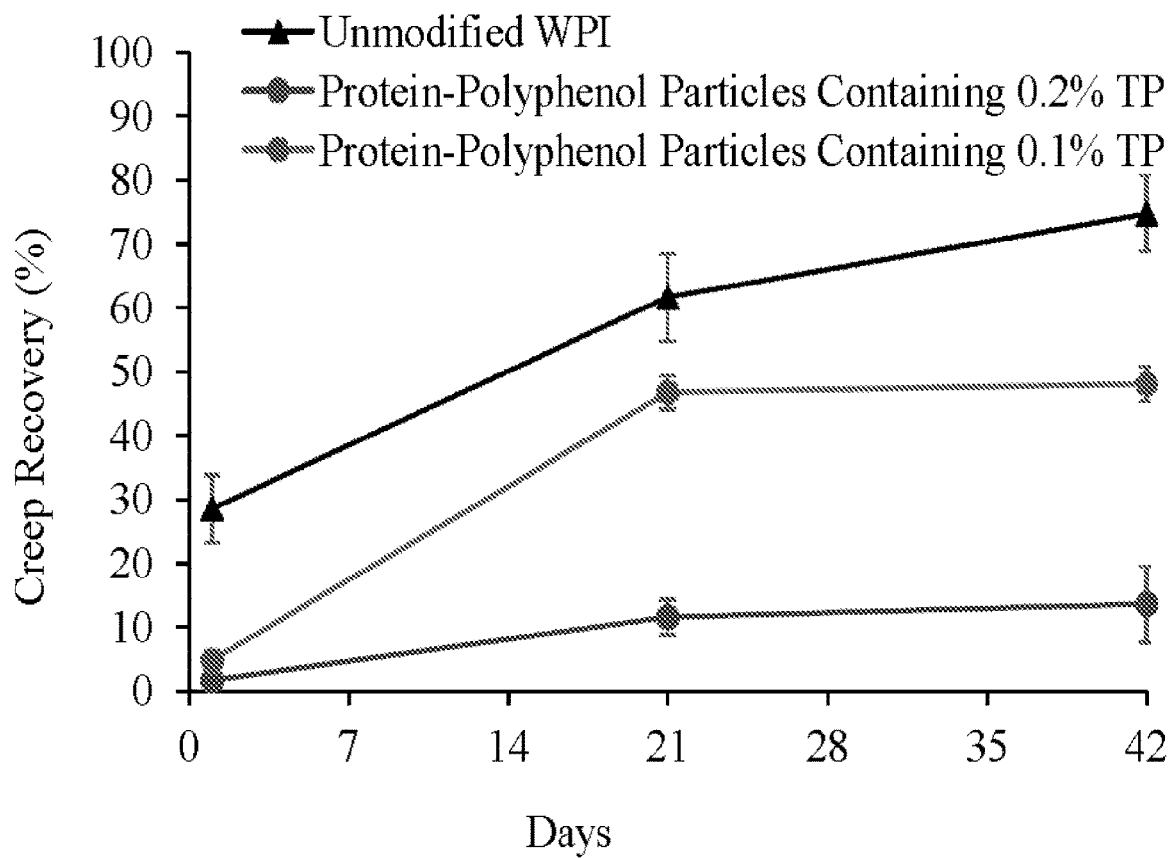
FIG. 10 shows percent creep recovery of whey protein-polyphenol aggregates containing various amounts of total polyphenols (TP). Overall, the structure-functionality of protein-polyphenol aggregate powders was evaluated in liquid, foam, and bar systems to prove feasibility of incorporation into various foods. Blackcurrant powders containing 1 and 5% phenolics had functionality equal or greater to that of whey protein isolate containing no polyphenolics in foam and liquid systems. Protein-polyphenol aggregate particles with cranberry polyphenols containing 0.1 or 0.2% polyphenols remained flexible, while bars produced with unmodified whey protein isolate became rigid.

Bars produced with whey protein isolate (WPI) had a smaller $J_{max}$ (were more rigid) than bars formulated with whey protein-cranberry polyphenol (WP-CP) particles (FIG. 9). Bars formed with the WP-CP had a reduced percent recovery compared to bars made with WPI alone (FIG. 10). Greater percent recovery indicates a more elastic system and possible network formation. Rheological properties are consistent with WP-CP particles acting as inactive fillers and preventing formation of a protein network. While these two examples use blackcurrant and cranberry polyphenols, use of polyphenol sources from other juices or with greater polyphenol amount are expected to behave in similar ways, depending on the polyphenolic profiles present in the donor tissues, with a concentration dependent effect.

The bars formulated with 0.2% TP (total phenol) WP-CP particles were extremely soft and sticky, reminiscent of an exercise goo or gel, and over time achieved a texture similar to a gummy or fruit leather. This ingredient could therefore be used in a non-bar exercise recovery product or used in higher concentrations in order to formulate a firmer bar structure. Results of the 0.1% TP WP-CP particles achieved an acceptable bar texture, and the protein-polyphenol aggregate-containing bars did not become as hard as those made with unmodified WPI.

The foregoing is illustrative of the invention, and is not to be construed as limiting thereof. The invention is defined by the following claims, with equivalents of the claims to be included therein.

REFERENCES

Alvarez, L. M., M. Sc. Thesis, Brock University, Ontario, Canada, 2010
Brudzynski, K.; Sjaarda, C. and Maldonado-Alvarez, L. (2013), PLoS ONE, 8, e72897
Charlton, A. J.; Baxter, N. J.; Khan, M. L.; Moir, A. J. G.; Chem., 50, 1593-1601

Grace, M.; Esposito, D.; Dunlap, K.; Lila, M. (2014), J. Agric. Food. Chem, 62, 4007-4017
Haslam, E. (1996), J. Nat. Prod., 59, 205-215
Haslam, E.; Davies, A. P. and Williamson, M. P. (2002), J. Agric. Food
Herald, T. J.; Gadgil, P.; Tilley, M. (2012), J. Sci. Food Agric., 92, 2326-2331
Ishii, T.; Mori, T.; Tanaka, T.; Mizuno, D.; Yamaji, R.; Kumazawa, S.; Nakayama, T.; Akagawa, M. (2008), Free Radic. Biol. Med., 45, 1384-1394
Li, Y., Szlachetka, K., Chen, P., Lin, X., Ruan, R. (2008), Cereal Chem. J. 85, 780-786.
Paz, M. A., Fluckiger, R., Boak, A., Kagan, H. M. & Gallop, P. M. Specific detection of quinoproteins by redox-cycling staining. J. Biol. Chem. 266, 689-692 (1991)
Plundrich, N.J.; White, B. L.; Dean, L. L.; Davis, J. P.; Foegeding, E. A.; Lila M. A. (2015), Food Funct., 6, 2145-2154
Sampath, T. K.; Coughlin, J. E.; Whetstone, R. M.; Banach, D.; Corbett, C.; Ridge, R. J.; Cjzkaynak, E.; Oppermann, H. and Rueger, D. J. (1990), J. Biol. Chem., 265, 13198-13205
Siebert, K. J. (1999), J. Agric. Food Chem., 47, 353-362
Singleton, V. L., Orthofer, R., and Lamuela-Raventós, R. M. (1999), Methods in Enzymology, (Elsevier), pp. 152-178
Wallace, T. C.; Giusti, M. M. (2010), J. Food Sci., 75, C619-C625

TABLE 1

Total phenol content in extracts[a,b]

| source | Total phenolic content mg/mL |
|---|---|
| blackcurrant extract[c] | 34.18 b |
| blueberry pomace extract | 3.36 c |
| cranberry pomace extract | 0.83 e |
| green tea leaves extract | 36.76 a |
| cinnamon powder extract | 2.38 d |

[a]Values within the column with different letters are significantly different at $p < 0.05$.
[b]expressed as mg per mL gallic acid equivalents;
[c]the blackcurrant extract was a highly concentrated, commercial sugar-free extract.

TABLE 2

Individual procyanidins in plant and berry extracts

| | concentration of individual procyanidins (mg mL$^{-1}$) in plant extracts | | | | | | |
|---|---|---|---|---|---|---|---|
| source | DP1 | DP2 | DP3 | DP4 | DP > 4 | polymers | total |
| blackcurrant extract | 0.13 b | 0.17 b | 0.24 b | 0.28 a | 0.81 a | 0.66 a | 2.29 a |
| blueberry pomace extract | 0.02 c | 0.08 c | 0.09 c | 0.09 b | 0.36 ab | 0.60 a | 1.24 b |
| cranberry pomace extract | 0.00 d | 0.02 d | 0.03 c | 0.03 c | 0.13 b | 0.26 b | 0.47 c |
| green tea leaves extract | 1.33 a | 0.55 a | 0.36 a | 0.14 b | 0.12 b | 0.05 c | 2.55 a |
| cinnamon powder extract | 0.01 d | 0.03 d | 0.31 ab | 0.22 a | 0.63 a | 0.06 c | 1.26 b |

DP, degree of polymerization;
DP1, monomers expressed as epicatechin;
DP2, dimers expressed as PAC A2;
DP3, trimers expressed as PAC C1;
DP4, tetramers expressed as PAC D;
DP > 4, oligomers expressed as PAC D;
polymers, expressed as PAC D

TABLE 3

Phenolic compounds identified in plant and berry extracts by LC-MS

| source | Rt (min) | MS (M-H)$^-$ m/z | MS-MS m/z | error (ppm) | tentative identification | molecular formula |
|---|---|---|---|---|---|---|
| green tea leaves extract | 18.0 | 289.0707 | 245, 203 | 3.8 | catechin | $C_{15}H_{14}O_6$ |
| | 23.4 | 289.0715 | 245, 203 | 4.5 | epicatechin | $C_{15}H_{14}O_6$ |
| | 4.8 | 305.0668 | 219 | 0.3 | epigallocatechin isomer 1 | $C_{15}H_{14}O_7$ |
| | 10.2 | 305.0653 | 219 | 4.6 | epigallocatechin isomer 2 | $C_{15}H_{14}O_7$ |
| | 19.6 | 337.0928 | 191 | 0.3 | 4-p-coumarolyquinic acid | $C_{16}H_{18}O_8$ |
| | 2.4 | 343.0670 | 191 | 0.3 | theogallin | $C_{14}H_{16}O_{10}$ |
| | 12.7 | 353.0887 | 191 | 2.6 | 3-caffeoylquinic acid | $C_{16}H_{18}O_9$ |
| | 23.8 | 441.0822 | 289, 245 | 1.1 | epicatechin gallate | $C_{22}H_{18}O_{10}$ |
| | 16.9 | 457.0773 | 193 | 0.7 | epigallocatechin gallate isomer 1 | $C_{22}H_{18}O_{11}$ |
| | 21.2 | 457.0782 | 193 | 1.3 | epigallocatechin gallate isomer 2 | $C_{22}H_{18}O_{11}$ |
| | 14.3 | 745.1423 | 407, 289 | 1.7 | epigallocatechin-epigallocatechin gallate | $C_{37}H_{30}O_{17}$ |
| | 31.3 | 447.0951 | 285, 255 | 4.0 | kaempferolglucoside | $C_{21}H_{20}O_{11}$ |
| | 29.5 | 463.0898 | 301, 271 | 3.5 | quercetin-3-O-hexoside | $C_{21}H_{20}O_{12}$ |
| | 22.4 | 471.0954 | 305, 269 | 4.5 | epigallocatechin methyl gallate | $C_{23}H_{20}O_{11}$ |
| | 26.4 | 479.0840 | 316, 271 | 1.9 | myricetin-3-O-hexoside | $C_{21}H_{20}O_{13}$ |
| | 34.3 | 563.1222 | 545 | 4.8 | theaflavin | $C_{29}H_{24}O_{12}$ |
| | 13.8 | 577.1353 | 407, 289 | 0.2 | PAC dimer B2 | $C_{30}H_{26}O_{12}$ |
| | 10.7 | 577.1367 | 407, 289 | 2.6 | PAC dimer B1 | $C_{30}H_{26}O_{12}$ |
| | 30.9 | 593.1506 | 285, 255 | 1.0 | kaempferol rutinoside | $C_{27}H_{30}O_{15}$ |
| | 28.9 | 593.0977 | 441, 293, 271 | 3.2 | kaepferol coumaryl glucoside | $C_{29}H_{22}O_{14}$ |
| | 25.8 | 609.0876 | 457, 305 | 1.6 | epigallocatechin digallate | $C_{29}H_{22}O_{15}$ |
| | 31.0 | 755.2063 | 285 | 3.1 | kaempferol glucosylrutinoside | $C_{33}H_{40}O_{20}$ |
| | 13.6 | 913.1493 | 457 | 2.6 | gallocatechin-gallate-dimer | $C_{44}H_{34}O_{22}$ |
| blackcurrant extract | 33.6 | 301.0358 | 212 | 1.3 | quercetin | $C_{15}H_{10}O_7$ |
| | 28.5 | 447.0918 | 285 | 3.7 | kaempferol-3-O-glucoside | $C_{21}H_{20}O_{11}$ |
| | 26.7 | 479.0841 | 316, 271 | 2.1 | myricetin-3-O-hexoside | $C_{21}H_{20}O_{13}$ |
| | 21.3 | 593.1517 | 285 | 0.8 | kaempferol hexose-deoxyhexoside | $C_{27}H_{30}O_{15}$ |

TABLE 3-continued

Phenolic compounds identified in plant and berry extracts by LC-MS

| source | Rt (min) | MS (M-H)⁻ m/z | MS-MS m/z | error (ppm) | tentative identification | molecular formula |
|---|---|---|---|---|---|---|
| | 29.8 | 609.1438 | 301, 271 | 3.8 | quercetin-3-O-rutinoside | $C_{27}H_{30}O_{16}$ |
| | 26.9 | 625.1397 | 316, 271 | 2.1 | myricetin-3-O-rutinoside | $C_{27}H_{30}O_{17}$ |
| | 5.3 | 609.1233 | 423 | 2.8 | epigallocatechin dimer | $C_{30}H_{26}O_{14}$ |
| | 9.0 | 897.1885 | 682, 285 | 3.8 | epigallocatechin-epigallocatechin-epicatechin | $C_{45}H_{38}O_{20}$ |
| cinnamon powder extract | multiple peaks | 575 | 289 | | PAC dimer A | $C_{30}H_{24}O_{12}$ |
| | 9.3 | 577.138 | 407, 289 | 4.9 | PAC dimer B1 | $C_{30}H_{26}O_{12}$ |
| | 14.4 | 577.1378 | 407, 289 | 4.5 | PAC dimer B2 | $C_{30}H_{26}O_{12}$ |
| | 15.0 | 1439.303 | 411, 289 | 0.7 | PAC pentamer A | $C_{75}H_{60}O_{30}$ |
| | multiple peaks | 863 | 541, 411, 289 | | PAC trimer A | $C_{45}H_{36}O_{18}$ |
| | multiple peaks | 865 | 407 | | PAC trimer B | $C_{45}H_{38}O_{18}$ |
| | 13.7 | 1151.236 | 573, 411 | 4.2 | PAC tetramer A | $C_{60}H_{48}O_{24}$ |
| cranberry pomace extract | 18.6 | 289.0695 | 245 | 2.4 | catechin | $C_{15}H_{14}O_6$ |
| | 33.8 | 301.0351 | 290, 271 | 1.0 | quercetin | $C_{15}H_{10}O_7$ |
| | 31.0 | 433.0786 | 300, 271 | 2.3 | quercetin 3-O-pentoside | $C_{20}H_{18}O_{11}$ |
| | 31.4 | 447.0972 | 301 | 4.5 | methoxyquercetin 3-xyloside | $C_{14}H_{24}O_{16}$ |
| | 29.3 | 463.0890 | 301 | 1.7 | quercetin 3-galactoside | $C_{21}H_{20}O_{12}$ |
| | 32.0 | 507.1169 | 344 | 4.9 | syringetin-3-O-glucoside | $C_{23}H_{24}O_{13}$ |
| | 34.7 | 567.1171 | 300, 271 | 2.8 | quercetin 3-benzoyl galactoside | $C_{28}H_{24}O_{13}$ |
| | 25.2 | 575.1194 | 423, 285 | 0.2 | PAC dimer A2 | $C_{30}H_{24}O_{12}$ |
| | 14.3 | 577.1377 | 407, 289 | 4.3 | PAC dimer B2 | $C_{30}H_{26}O_{12}$ |
| | 9.2 | 577.1367 | 407, 289 | 2.6 | PAC dimer B1 | $C_{30}H_{26}O_{12}$ |
| | 33.7 | 609.1225 | 463, 301 | 4.1 | quercetin 3-coumaroylgalactoside | $C_{30}H_{26}O_{14}$ |
| | 11.6 | 1439.303 | 575, 405, 285 | 1.1 | PAC pentamer A | $C_{75}H_{60}O_{30}$ |
| | 17.5 | 863.1847 | 575, 423 | 2.1 | PAC trimer A | $C_{45}H_{36}O_{18}$ |
| | 19.9 | 865.1993 | 577, 407 | 0.9 | PAC trimer B | $C_{45}H_{38}O_{18}$ |
| | 6.4 | 1151.248 | 711, 411 | 4.6 | PAC tetramer A | $C_{60}H_{48}O_{24}$ |
| blueberry pomace extract | 18.4 | 289.0717 | 245 | 0.4 | catechin | $C_{15}H_{14}O_6$ |
| | 33.5 | 301.0360 | 229 | 2.0 | quercetin | $C_{15}H_{10}O_7$ |
| | 30.7 | 317.0290 | 316, 256 | 4.1 | myricetin | $C_{15}H_{10}O_8$ |
| | 13.2 | 353.0872 | 191 | 1.7 | chlorogenic acid | $C_{16}H_{18}O_9$ |
| | 30.9 | 433.0799 | 300, 271 | 2.3 | quercetin 3-O-pentoside | $C_{20}H_{18}O_{11}$ |
| | 31.2 | 447.0973 | 301, 255 | 4.3 | methoxyquercetin 3-xyloside | $C_{21}H_{20}O_{11}$ |
| | 29.8 | 477.0690 | 301 | 3.1 | quercetin 3-O-glucuronide | $C_{21}H_{18}O_{13}$ |
| | 26.3 | 479.0847 | 479, 299 | 3.3 | myricetin 3-O-hexoside | $C_{21}H_{20}O_{13}$ |
| | 32.0 | 507.1162 | 344, 273 | 3.6 | syringetin-3-O-glucoside | $C_{23}H_{24}O_{13}$ |
| | 9.1 | 577.1358 | 407, 289 | 1.0 | PAC dimer B1 | $C_{30}H_{26}O_{12}$ |
| | 25.2 | 575.1230 | 423, 285 | 4.5 | PAC dimer A | $C_{30}H_{24}O_{12}$ |
| | 14.2 | 577.1365 | 407, 289 | 2.3 | PAC dimer B2 | $C_{30}H_{26}O_{12}$ |
| | 15.7 | 863.1899 | 711, 411 | 2.8 | PAC trimer A | $C_{45}H_{36}O_{18}$ |
| | 9.9 | 1153.259 | 865, 449 | 2.6 | PAC tetramer B | $C_{60}H_{50}O_{24}$ |

Rt, retention time;
PAC, proanthocyanidin

The invention claimed is:

1. A protein-polyphenol aggregate matrix comprising polyphenols covalently bound to proteins,
wherein the polyphenols are present in the protein-polyphenol aggregate matrix at a concentration of at least 15% (w/w).

2. The protein-polyphenol aggregate matrix of claim 1, wherein the proteins are from peanut, tree nut, milk, whey, egg, soy, fish, shellfish, rice, wheat, or any combination thereof.

3. The protein-polyphenol aggregate matrix of claim 1, wherein the protein-polyphenol aggregate matrix is an immunotherapeutic protein product comprising at least about 15% polyphenols (w/w).

4. A method of producing the protein-polyphenol aggregate matrix of claim 1, the method comprising:
contacting a concentrated polyphenol extract with the proteins to produce a covalently bonded protein-polyphenol complexed product, wherein the polyphenol extract has at least 15% polyphenols (w/w) and has less than 10% (w/w) sugars; and
dehydrating the protein-polyphenol complexed product to produce the protein-polyphenol aggregate matrix of claim 1.

5. The method of claim 4, wherein the dehydrating is simultaneous with contacting.

6. The method of claim 4, wherein the protein-polyphenol aggregate matrix is a dry granular aggregate.

7. The method of claim 4, wherein the concentration of polyphenols in the protein-polyphenol aggregate matrix is about 15 percent to about 75 percent of the weight of the total aggregate.

8. A method of attenuating an allergic response in a subject in need thereof, comprising administering to the subject the protein-polyphenol aggregate matrix of claim 1.

9. The protein-polyphenol aggregate matrix of claim 1, wherein the proteins comprise allergenic epitopes and wherein the polyphenols of the protein-polyphenol aggregate matrix mask or change the conformation of the allergenic epitopes, thereby rendering the proteins less allergenic relative to unmodified proteins.

10. The protein-polyphenol aggregate matrix of claim 1, wherein the protein-polyphenol aggregate matrix comprises less than 10% by weight sugars.

11. The protein-polyphenol aggregate matrix of claim 1, wherein the protein-polyphenol aggregate matrix is present as a dry granular aggregate.

12. The protein-polyphenol aggregate matrix of claim 1, wherein the concentration of polyphenols in the protein-polyphenol aggregate matrix is about 30 percent to about 75 percent of the weight of the total aggregate.

13. The protein-polyphenol aggregate matrix of claim 2, wherein the protein is a whey, egg, peanut and/or soy protein.

14. The protein-polyphenol aggregate matrix of claim 2, wherein the protein is a whey protein.

15. The protein-polyphenol aggregate matrix of claim 1, wherein the polyphenols are obtained from a fruit pomace.

16. The protein-polyphenol aggregate matrix of claim 1, wherein polyphenols are obtained from one or more of an apple, pomegranate, black current, blueberry, cranberry, blueberry, lingonberry, cherry, grape, muscadine, blackberry, chockberry, cinnamon, *Sorbaronia mitschurinii*, *Camellia* spp., and peanut.

17. The method of claim 8, wherein the concentration of polyphenols in the protein-polyphenol aggregate matrix is about 30 percent to about 75 percent of the weight of the total aggregate.

18. The method of claim 8, wherein the proteins comprise allergenic epitopes and wherein the polyphenols of the protein-polyphenol aggregate matrix mask or change the conformation of the allergenic epitopes, thereby rendering the proteins less allergenic relative to unmodified proteins.

19. The method of claim 8, wherein the protein-polyphenol aggregate matrix is present in a food product.

20. A food product comprising the protein-polyphenol aggregate matrix of claim 1.

* * * * *

UNITED STATES PATENT AND TRADEMARK OFFICE
CERTIFICATE OF CORRECTION

PATENT NO. : 11,452,706 B2
APPLICATION NO. : 15/524087
DATED : September 27, 2022
INVENTOR(S) : Lila et al.

It is certified that error appears in the above-identified patent and that said Letters Patent is hereby corrected as shown below:

In the Specification

Column 25, Line 25: Please delete "$\tau = \dfrac{M_o}{\left[\left(\dfrac{h}{d}\right) + \dfrac{1}{9}\right]\left(\dfrac{\pi d^3}{2}\right)}$," and replace with the following:

$$\tau = \dfrac{M_o}{\left[\left(\dfrac{h}{d}\right) + \dfrac{1}{6}\right]\left(\dfrac{\pi d^3}{2}\right)}$$

Signed and Sealed this
Twenty-first Day of February, 2023

*Katherine Kelly Vidal*

Katherine Kelly Vidal
*Director of the United States Patent and Trademark Office*